US012806283B2

(12) United States Patent
Moon et al.

(10) Patent No.: US 12,806,283 B2
(45) Date of Patent: *Nov. 24, 2026

(54) SONOSENSITIVE LIPOSOME AND METHOD FOR PREPARING SAME

(71) Applicant: IMGT CO, LTD., Gyeonggi-do (KR)

(72) Inventors: Hyungwon Moon, Gyeonggi-do (KR); Woo Young Yoo, Gyeonggi-do (KR); Yoonseok Kim, Gyeonggi-do (KR); Hyun Ryoung Kim, Gyeonggi-do (KR); Eun Ah Jung, Seoul (KR)

(73) Assignee: IMGT CO, LTD., Gyeonggi-do (KR)

( * ) Notice: Subject to any disclaimer, the term of this patent is extended or adjusted under 35 U.S.C. 154(b) by 637 days.

This patent is subject to a terminal disclaimer.

(21) Appl. No.: 17/997,384

(22) PCT Filed: Apr. 2, 2021

(86) PCT No.: PCT/KR2021/004131

§ 371 (c)(1),
(2) Date: Oct. 28, 2022

(87) PCT Pub. No.: WO2021/221330

PCT Pub. Date: Nov. 4, 2021

(65) Prior Publication Data

US 2023/0263905 A1 Aug. 24, 2023

(30) Foreign Application Priority Data

Apr. 29, 2020 (KR) ........................ 10-2020-0052356
Apr. 1, 2021 (KR) ........................ 10-2021-0042529

(51) Int. Cl.

| | |
|---|---|
| ***A61K 47/69*** | (2017.01) |
| ***A61K 47/28*** | (2006.01) |
| ***A61K 47/68*** | (2017.01) |
| ***A61P 35/00*** | (2006.01) |

(52) U.S. Cl.

CPC .......... *A61K 47/6911* (2017.08); *A61K 47/28* (2013.01); *A61K 47/6803* (2017.08); *A61P 35/00* (2018.01)

(58) Field of Classification Search

CPC ................ A61K 47/6911; A61K 47/28; A61K 47/6803; A61K 9/1271; A61K 31/704; A61K 41/0028; A61K 45/06; A61K 47/24; A61P 35/00

See application file for complete search history.

(56) References Cited

U.S. PATENT DOCUMENTS

| | | | | |
|---|---|---|---|---|
| 7,273,620 B1 * | 9/2007 | Zhigaltsev | ........... A61K 9/1272 | 424/450 |
| 2006/0127467 A1 | 6/2006 | Watkin | | |

FOREIGN PATENT DOCUMENTS

| | | |
|---|---|---|
| JP | 2008100956 | 5/2008 |
| KR | 20180031869 | 3/2018 |

OTHER PUBLICATIONS

Evjen. Sonosensitive liposomes for ultrasound-mediated drug delivery. Ph.D. Thesis, UiT Munin. 2011, pp. 1-51. (Year: 2011).*

Hauser. Chemistry and Physics of Lipids. 1987; 43(4): 283-299. (Year: 1987).*

Evjen Tove Julie, "Sonosensitive liposomes for ultrasound-mediated drug delivery", Ph.D. thesis, UIT Munin, (Apr. 1, 2011), XP055861333, 71 pages.

Fuse Toshiki, Tatsuaki Tagami, Masafumi Tane, Tetsuya Ozeki, "Effective light-triggered contents release from helper lipid-incorporated liposomes co-encapsulating gemcitabine and a water-soluble photosensitizer", International Journal of Pharmaceutics, (Apr. 5, 2018), vol. 540, doi:10.1016/j.ijpharm.2018.01.040, pp. 50-56, XP055861343.

International Search Report dated Jul. 13, 2021 for International Application No. PCT/KR2021/004131. 3 pages.

* cited by examiner

*Primary Examiner* — David Browe
(74) *Attorney, Agent, or Firm* — Riverside Law LLP

(57) ABSTRACT

The present invention relates to sonosensitive liposomes comprising 1,2-distearoyl-sn-glycero-3-phosphorylcholine (DSPC), 1,2-distearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), cholesterol, and lyso-PC, methods for preparing same, and methods of use thereof.

8 Claims, 11 Drawing Sheets

SONOSENSITIVE LIPOSOME AND METHOD FOR PREPARING SAME

CROSS-REFERENCE TO RELATED APPLICATIONS

This application is a national phase application filed under 35 U.S.C. § 371 claiming benefit to International Patent Application No. PCT/KR2021/004131, filed Apr. 2, 2021, which claims the benefit of priority from Korean Patent Application No. 10-2020-0052356, filed Apr. 29, 2020, and Korean Patent Application No. 10-2021-0042529, filed Apr. 1, 2021, the contents of each of which are hereby incorporated by reference in their entirety.

TECHNICAL FIELD

The present invention relates to a sonosensitive liposome and a method for preparing the same.

BACKGROUND ART

Cancer is one of the incurable diseases that human beings have to address, and huge capital is being invested in the development of drug to cure it all over the world. In Korea, as the number one disease cause of death, more than 100,000 people are diagnosed annually, and more than 60,000 people die.

Cancer treatment methods clinically used up to date include chemotherapy, radiation, targeted therapies, methods of excising a lesion by surgery, and the like. Representative examples of chemotherapeutic agents for anticancer treatment used to date include doxorubicin or adriamycin, cisplatin, Taxol, 5-fluorouracil, and the like, and have been widely used in the chemotherapy for the treatment of cancer. However, the methods have limitations, and do not completely cure the diseases but cause severe side effects and pain in patients. Therefore, there is a need for development of cancer treatment technology capable of minimizing the side effects.

Meanwhile, a liposome is a vesicle that is composed of phospholipids and derivatives thereof. The phospholipids and derivatives thereof spontaneously form vesicles when they are dispersed in water, and are characterized by a lipid bilayer enclosing the nucleus composed of an aqueous phase. Various liposomes have been used as carriers for therapeutic agents, such as drugs, enzymes, gene sequences, and the like, in the fields of medicine, pharmaceuticals, and biochemistry.

Accordingly, the present inventors have fused ultrasound technology with liposome technology to develop a novel method of treating cancer, which is still not known in cancer-related research and development fields such as cancer diagnosis and treatment, and the like.

DISCLOSURE

Technical Problem

The present inventors have developed a sonosensitive liposome having an excellent drug release rate and superior stability.

More specifically, the present inventors have found that, when ultrasound is applied to a drug-containing liposome with by fusion of ultrasound technology, the drug-containing liposome has a high drug release rate and an excellent antitumor effect and also exhibits superior blood stability compared to when the drug-containing liposome is not treated with ultrasound. Therefore, the present invention has been completed based on the above facts.

Therefore, it is an aspect of the present invention to provide a sonosensitive liposome preparation including 1,2-distearoyl-sn-glycero-3-phosphorylcholine (DSPC), 1,2-distearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), and lyso-PC.

It is another aspect of the present invention to provide a sonosensitive liposome preparation including 1,2-distearoyl-sn-glycero-3-phosphorylcholine (DSPC), 1,2-distearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), cholesterol, and lyso-PC.

It is still another aspect of the present invention to provide a pharmaceutical composition for preventing or treating cancer, which includes the sonosensitive liposome preparation.

It is yet another aspect of the present invention to provide a composition for drug delivery, which includes a liposome having a drug encapsulated therein as an active ingredient, wherein the liposome includes DSPC, DSPE-mPEG2000, DOPE, and lyso-PC; or includes DSPC, DSPE-mPEG2000, DOPE, cholesterol, and lyso-PC.

It is yet another aspect of the present invention to provide a method for preparing the sonosensitive liposome.

However, the technical objects of the present invention are not limited thereto, and other objects of the present invention which are not stated herein will become more apparent to those of ordinary skill in the art by describing in detail exemplary embodiments thereof.

Technical Solution

According to an aspect of the present invention, there is provided a sonosensitive liposome preparation which includes:

1,2-di stearoyl-sn-glycero-3-phosphorylcholine (DSPC), 1,2-di stearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), and lyso-PC; or 1,2-di stearoyl-sn-glycero-3-phosphorylcholine (DSPC), 1,2-di stearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), cholesterol, and lyso-PC.

According to another aspect of the present invention, there is provided a pharmaceutical composition for preventing or treating cancer, which includes the sonosensitive liposome preparation.

According to still another aspect of the present invention, there is provided a composition for drug delivery, which includes a sonosensitive liposome having a drug encapsulated therein as an active ingredient, wherein the liposome includes DSPC, DSPE-mPEG2000, DOPE, and lyso-PC; or includes DSPC, DSPE-mPEG2000, DOPE, cholesterol, and lyso-PC.

According to yet another aspect of the present invention, there is provided a method of preparing the sonosensitive liposome, which includes one preparation process selected from the group consisting of the following Preparation Processes 1 to 3:

[Preparation Process 1]

(a) dissolving DSPC, DSPE-mPEG2000, DOPE, and lyso-PC in a first organic solvent;

(b) evaporating the organic solvent to prepare a liposome membrane;

(c) hydrating the liposome membrane in an aqueous solution and stirring the liposome membrane solution; and (d) extruding the liposome membrane solution through an extruder.

[Preparation Process 2]

(a) dissolving DSPC, DSPE-mPEG2000, DOPE, and lyso-PC in ethanol;

(b) hydrating the ethanol solution prepared in Step (a) in an aqueous solution and stirring the ethanol solution; and (c) extruding the ethanol solution through an extruder.

[Preparation Process 3]

(a) dissolving DSPC, DSPE-mPEG2000, DOPE, and lyso-PC in a first organic solvent;

(b) mixing the first organic solvent solution prepared in Step (a) and an aqueous solution while changing the flow velocities thereof using a channel of a microfluidic system; and (c) removing the organic solvent.

According to yet another aspect of the present invention, there is provided a method of treating cancer, which includes: administering an effective amount of the sonosensitive liposome preparation to a subject; and treating the sonosensitive liposome preparation with ultrasound.

According to yet another aspect of the present invention, there is provided a use of the sonosensitive liposome preparation for cancer treatment.

According to yet another aspect of the present invention, there is provided a use of the sonosensitive liposome preparation for the production of a cancer therapeutic agent.

According to yet another aspect of the present invention, there is provided a method of delivering a drug, which includes: administering an effective amount of a liposome having a drug encapsulated therein to a subject, wherein the liposome includes DSPC, DSPE-mPEG2000, DOPE, and lyso-PC.

According to yet another aspect of the present invention, there is provided a use of the liposome having the drug encapsulated therein for drug delivery, wherein the liposome includes DSPC, DSPE-mPEG2000, DOPE, and lyso-PC.

According to yet another aspect of the present invention, there is provided a use of the liposome having the drug encapsulated therein for the preparation of a drug delivery carrier, wherein the liposome includes DSPC, DSPE-mPEG2000, DOPE, and lyso-PC.

According to one exemplary embodiment of the present invention, the DSPC, the DSPE-mPEG2000, the DOPE, the cholesterol, and the lyso-PC may be included at a molar ratio (mol %) of 1 to 50:1 to 10:5 to 80:0.1 to 50:0.1 to 20, but the present invention is not limited thereto.

According to another exemplary embodiment of the present invention, the DSPC may be included at 0.1 to 50% by dry weight based on the total weight of the liposome preparation, the DSPE-mPEG2000 may be included at 3 to 50% by dry weight based on the total weight of the liposome preparation, the DOPE may be included at 1 to 80% by dry weight based on the total weight of the liposome preparation, the cholesterol may be included at 0.05 to 40% by dry weight based on the total weight of the liposome preparation, and the lyso-PC may be included at 0.5 to 10% by dry weight based on the total weight of the liposome preparation, but the present invention is not limited thereto.

According to still another exemplary embodiment of the present invention, the liposome membrane of the sonosensitive liposome preparation may be composed of DSPC, DSPE-mPEG2000, DOPE, cholesterol, and lyso-PC, but the present invention is not limited thereto.

According to yet another exemplary embodiment of the present invention, the sonosensitive liposome preparation may have a drug encapsulated therein, but the present invention is not limited thereto.

According to yet another exemplary embodiment of the present invention, the drug may be an anticancer drug, and may, for example, include one or more selected from the group consisting of doxorubicin, paclitaxel, doxetaxel, cisplatin, Gleevec, 5-fluorouracil (5-FU), tamoxifen, carboplatin, topotecan, belotecan, imatinib, irinotecan, floxuridine, vinorelbine, gemcitabine, leuprolide, flutamide, zoledronate, methotrexate, camptothecin, vincristine, hydroxyurea, streptozotocin, valrubicin, retinoic acid, mechlorethamine, chlorambucil, busulfan, doxifluridine, vinblastine, mitomycin, prednisone, Afinitor, and mitoxantrone, but the present invention is not limited thereto.

According to yet another exemplary embodiment of the present invention, the sonosensitive liposome preparation may have ensured stability, and the stability may be blood stability, but the present invention is not limited thereto.

According to yet another exemplary embodiment of the present invention, the sonosensitive liposome preparation may have one or more of the following characteristics, but the present invention is not limited thereto i. a particle size of 100 nm to 200 nm; and ii. a drug encapsulation efficiency of 50% to 100%.

According to yet another exemplary embodiment of the present invention, the sonosensitive liposome preparation, or a pharmaceutical composition including the same may be administered sequentially or concurrently with sonication, but the present invention is not limited thereto.

According to yet another exemplary embodiment of the present invention, the cancer may include one or more selected from the group consisting of breast cancer, colon cancer, lung cancer, small-cell lung cancer, gastric cancer, liver cancer, blood cancer, bone cancer, pancreatic cancer, skin cancer, head cancer, neck cancer, skin melanoma, intraocular melanoma, uterine cancer, ovarian cancer, rectal cancer, anal cancer, colorectal cancer, fallopian tube carcinoma, endometrial carcinoma, cervical cancer, vaginal cancer, vulva carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureteral cancer, renal cell carcinoma, renal pelvic carcinoma, CNS tumors, primary CNS lymphoma, spinal cord tumors, brainstem glioma, and pituitary adenoma, but the present invention is not limited thereto.

According to yet another exemplary embodiment of the present invention, in Step (a), cholesterol may be further added and dissolved therein, but the present invention is not limited thereto.

According to yet another exemplary embodiment of the present invention, the organic solvent may include one or more selected from the group consisting of dimethylacetamide, dimethylformamide, dimethyl sulfoxide, chloroform, methanol, ethanol, and ether, but the present invention is not limited thereto.

Advantageous Effects

The present inventors have found that a sonosensitive liposome according to the present invention has high encapsulation efficiency and excellent drug stability and liposome preparation stability, and shows an excellent effect of increasing a drug release rate by sonication compared to the existing commercial drugs, as well as a cancer cell death effect and a cancer cell-penetrating effect. Therefore, the sonosensitive liposome according to the present invention increases delivery efficiency of an encapsulated drug, and has an improved drug delivery effect when used in combination with sonication to target cancer cells. As a result, the sonosensitive liposome according to the present invention is expected to shows various functions in the fields of cancer treatment and drug delivery carriers.

BEST MODE

Figure 1:
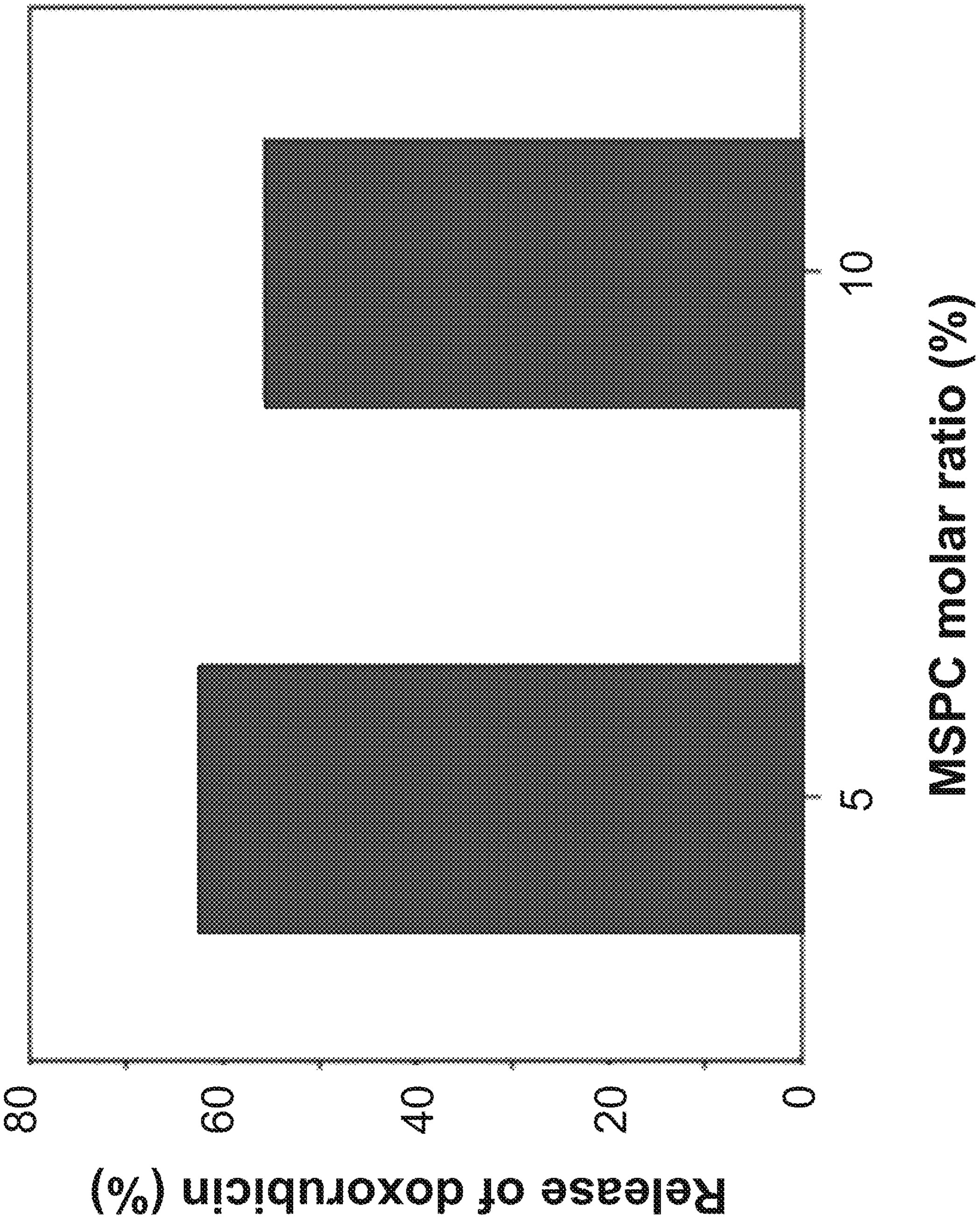
FIG. 1 is a diagram showing a release rate of doxorubicin by the ultrasound sensitization of a liposome according to the ratio of 1-stearoyl-2-hydroxy-sn-glycero-3-phosphocholine (MSPC) according to one exemplary embodiment of the present invention.

The present invention provides a sonosensitive liposome preparation which includes 1,2-distearoyl-sn-glycero-3-phosphorylcholine (DSPC), 1,2-distearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), and lyso-PC.

The preparation of the present invention may further include cholesterol.

The term "DSPC" used in the present invention is an abbreviated form of 1,2-distearoyl-sn-glycero-3-phosphocholine, and refers to a phospholipid which is composed of two palmitic acid residues attached to a phosphatidylcholine head group.

The term "DSPE-mPEG2000" used in the present invention is an abbreviated form of 1,2-distearoyl-sn-glycero-3-phosphoethanol amine with conjugated methoxyl poly(ethylene glycol 2000), and refers to a pegylated derivative of 1,2-distearoyl-sn-glycero-3-PE (DSPE).

The term "DOPE" used in the present invention is an abbreviated form of 1,2-dioleoyl-sn-glycero-3-phosphoethanolamine, and is known to form a heterogeneous liposome with DOTAP used as a delivery vehicle for a therapeutic agent.

The term "cholesterol" used in the present invention refers to one of steroid compounds. The cholesterol includes cholesterol derivatives. The cholesterol derivatives may be, for example, sitosterol, ergosterol, stigmasterol, 4,22-stigmastadien-3-one, stigmasterol acetate, lanosterol, cycloartenol, or a combination thereof. Cholesterol is positioned in a lipid bilayer, and its amount is adjusted to lower or increase permeability. In this case, the cholesterol may be used regardless of its own ratio in a liposome preparation The term "lyso-PC" used in the present invention is an abbreviated form of lysophosphatidylcholine, which is a representative term of a lipid composed of an acyl chain derived from phosphocholine consisting of choline as a head group, and includes various types of lyso-PC.

In the present invention, the lyso-PC may be represented by the following Formula 1, but the present invention is not limited thereto.

[Formula 1]

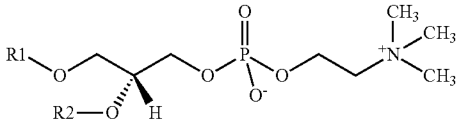

(wherein R1 and/or R2 are a $C_6$ to $C_{26}$ acyl group, a $C_6$ to $C_{26}$ alkyl group, a $C_6$ to $C_{26}$ alkenyl group, a $C_6$ to $C_{26}$ alkynyl group, a substituted or unsubstituted $C_6$ to $C_{26}$ cycloalkyl, a substituted or unsubstituted $C_6$ to $C_{26}$ aryl group, a substituted or unsubstituted $C_7$ to $C_{26}$ arylalkyl group, or H).

In the present invention, the acyl group may be an aromatic carboxylic acid residue, a saturated fatty acid residue, or an unsaturated fatty acid residue, but the present invention is not limited thereto.

In the present invention, the lyso-PC represented by Formula 1 may be more particularly represented by the following Formula 2 or 3, but the present invention is not limited thereto.

In the present invention, the lyso-PC may be 1-lysophosphatidylcholine (LPC) or 2-LPC represented by the following Formula 2 or 3, but the present invention is not limited thereto.

[Formula 2]

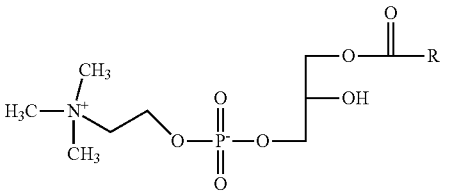

[Formula 3]

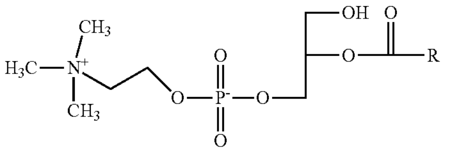

(wherein R is a $C_6$ to $C_{26}$ alkyl group, a $C_6$ to $C_{26}$ alkenyl group, a $C_6$ to $C_{26}$ alkynyl group, a substituted or unsubstituted $C_6$ to $C_{26}$ cycloalkyl, a substituted or unsubstituted $C_6$ to $C_{26}$ aryl group, a substituted or unsubstituted $C_7$ to $C_{26}$ arylalkyl group, or H).

In the present invention, the lyso-PC may include one or more selected from the group consisting of lyso-PC (6:0), lyso-PC (7:0), lyso-PC (8:0), lyso-PC (9:0), lyso-PC (10:0), lyso-PC (11:0), lyso-PC (12:0), lyso-PC (13:0), lyso-PC (14:0), lyso-PC (15:0), lyso-PC (16:0), 2-lyso-PC (16:0), lyso-PC (17:0), lyso-PC (17:1), lyso-PC (18:0), lyso-PC (18:1), lyso-PC (18:2), 2-lyso-PC (18:0), 2-lyso-PC (18:1), lyso-PC (19:0), lyso-PC (20:1), lyso-PC (20:4), lyso-PC (22:0), lyso-PC (22:5), lyso-PC (24:0), lyso-PC (26:0), and lyso-PC (20:5), but the present invention is not limited thereto.

In the present invention, the DSPC, the DSPE-mPEG2000, the DOPE, and the lyso-PC may be included at a molar ratio (mol %) of 1 to 50:1 to 10:5 to 80:0.1 to 20, but the present invention is not limited thereto.

According to another exemplary embodiment of the present invention, the DSPC may be included at 0.1 to 50% by dry weight based on the total weight of the liposome preparation, the DSPE-mPEG2000 may be included at 3 to 50% by dry weight based on the total weight of the liposome preparation, the DOPE may be included at 1 to 80% by dry weight based on the total weight of the liposome preparation, and the lyso-PC may be included at 0.5 to 10% by dry weight based on the total weight of the liposome preparation, but the present invention is not limited thereto.

Also, in the present invention, the DSPC, the DSPE-mPEG2000, the DOPE, the cholesterol, and the lyso-PC may be included at a molar ratio (mol %) of 1 to 50:1 to 10:5 to 80:0.1 to 50:0.1 to 20, a molar ratio (mol %) of 1 to 40:1 to 9:35 to 80:0.1 to 40:1 to 10, a molar ratio (mol %) of 10 to 40:3 to 7:40 to 65:0.1 to 45:0.1 to 10, a molar ratio (mol %) of 0.1 to 20:1 to 8:63 to 67:0.1 to 30:3 to 10, a molar ratio (mol %) of 5 to 15:2 to 7:64 to 67:10 to 30:3 to 10, a molar ratio (mol %) of 5 to 15:3 to 6:64 to 66:15 to 30:5 to 10, a molar ratio (mol %) of 0.1 to 20:1 to 8:53 to 57:0.1 to 30:5 to 10, a molar ratio (mol %) of 5 to 15:2 to 7:54 to 57:3 to 20:5 to 10, or a molar ratio (mol %) of 5 to 15:3 to 6:54 to 56:5 to 10:5 to 10, but the present invention is not limited thereto.

Also, in the present invention, the DSPC may be included at a 1 to 50 molar ratio (mol %), a 5 to 50 molar ratio (mol %), a 5 to 40 molar ratio (mol %), a 5 to 35 molar ratio (mol %), a 5 to 30 molar ratio (mol %), a 5 to 25 molar ratio (mol %), a 5 to 20 molar ratio (mol %), a 5 to 15 molar ratio (mol %), a 7 to 12 molar ratio (mol %), a 25 to 35 molar ratio (mol %), a 27 to 32 molar ratio (mol %), or a 35 to 45 molar ratio (mol %) based on the total weight of the liposome preparation, but the present invention is not limited thereto.

Also, in the present invention, the DSPE-mPEG2000 may be included at a 1 to 10 molar ratio (mol %), a 2 to 9 molar ratio (mol %), a 3 to 8 molar ratio (mol %), a 3 to 7 molar ratio (mol %), or a 4 to 6 molar ratio (mol %) based on the total weight of the liposome preparation, but the present invention is not limited thereto.

Also, in the present invention, the DOPE may be included at a 5 to 80 molar ratio (mol %), a 5 to 70 molar ratio (mol %), a 10 to 70 molar ratio (mol %), a 20 to 70 molar ratio (mol %), a 30 to 70 molar ratio (mol %), a 40 to 70 molar ratio (mol %), or a 40 to 65 molar ratio (mol %) based on the total weight of the liposome preparation, but the present invention is not limited thereto.

Also, in the present invention, the cholesterol may be included at a 0.1 to 50 molar ratio (mol %), a 0.1 to 45 molar ratio (mol %), a 1 to 45 molar ratio (mol %), a 5 to 45 molar ratio (mol %), a 5 to 40 molar ratio (mol %), a 5 to 35 molar ratio (mol %), a 5 to 30 molar ratio (mol %), a 5 to 25 molar ratio (mol %), a 5 to 20 molar ratio (mol %), a 5 to 15 molar ratio (mol %), a 10 to 40 molar ratio (mol %), a 10 to 30 molar ratio (mol %), a 10 to 25 molar ratio (mol %), a 10 to 20 molar ratio (mol %), a 20 to 40 molar ratio (mol %), a 30 to 40 molar ratio (mol %), a 5 to 10 molar ratio (mol %), or a 40 to 50 molar ratio (mol %) based on the total weight of the liposome preparation, but the present invention is not limited thereto.

Also, in the present invention, the lyso-PC may be included at a 0.1 to 20 molar ratio (mol %), a 0.1 to 15 molar ratio (mol %), a 0.1 to 10 molar ratio (mol %), a 1 to 20 molar ratio (mol %), a 3 to 20 molar ratio (mol %), a 3 to 15 molar ratio (mol %), a 3 to 10 molar ratio (mol %), a 3 to 7 molar ratio (mol %), a 5 to 20 molar ratio (mol %), a 5 to 15 molar ratio (mol %), a 5 to 10 molar ratio (mol %), a 7 to 20 molar ratio (mol %), a 7 to 15 molar ratio (mol %), a 7 to 12 molar ratio (mol %), a 8 to 12 molar ratio (mol %), a 9 to 11 molar ratio (mol %), a 4 to 6 molar ratio (mol %), or a 6 to 8 molar ratio (mol %) based on the total weight of the liposome preparation, but the present invention is not limited thereto.

Also, in the present invention, the DSPC may be included at 0.1 to 50% by dry weight based on the total weight of the liposome preparation, the DSPE-mPEG2000 may be included at 3 to 50% by dry weight based on the total weight of the liposome preparation, the DOPE may be included at 1 to 80% by dry weight based on the total weight of the liposome preparation, the cholesterol may be included at 0.05 to 40% by dry weight based on the total weight of the liposome preparation, and the lyso-PC may be included at 0.5 to 10% by dry weight based on the total weight of the liposome preparation, but the present invention is not limited thereto.

In the present invention, the DSPC may be included at 0.1 to 50% by dry weight, 0.1 to 45% by dry weight, 0.1 to 40% by dry weight, 1 to 40% by dry weight, 1 to 30% by dry weight, 1 to 20% by dry weight, 1 to 15% by dry weight, 1 to 13% by dry weight, 3 to 20% by dry weight, 5 to 20% by dry weight, 7 to 20% by dry weight, 5 to 15% by dry weight, 7 to 13% by dry weight, or 9 to 11% by dry weight based on the total weight of the liposome preparation, but the present invention is not limited thereto.

In the present invention, the DSPE-mPEG2000 may be included at 3 to 50% by dry weight, 5 to 40% by dry weight, 10 to 30% by dry weight, 10 to 25% by dry weight, 10 to 20% by dry weight, 15 to 30% by dry weight, 15 to 25% by dry weight, 15 to 20% by dry weight, 16 to 19% by dry weight, or 17 to 19% by dry weight based on the total weight of the liposome preparation, but the present invention is not limited thereto.

In the present invention, the cholesterol may be included at 0.05 to 40% by dry weight, 1 to 40% by dry weight, 1 to 30% by dry weight, 1 to 20% by dry weight, 1 to 15% by dry weight, 1 to 13% by dry weight, 1 to 10% by dry weight, 3 to 20% by dry weight, 3 to 15% by dry weight, 3 to 13% by dry weight, 3 to 10% by dry weight, 5 to 20% by dry weight, 5 to 15% by dry weight, 5 to 13% by dry weight, 5 to 10% by dry weight, 6 to 8% by dry weight, 10 to 40% by dry weight, 10 to 35% by dry weight, 10 to 30% by dry weight, 10 to 25% by dry weight, 10 to 20% by dry weight, 15 to 40% by dry weight, 15 to 30% by dry weight, 15 to 25% by dry weight, 15 to 22% by dry weight, or 20 to 30% by dry weight based on the total weight of the liposome preparation, but the present invention is not limited thereto.

In the present invention, the DOPE may be included at 1 to 80% by dry weight, 5 to 80% by dry weight, 10 to 80% by dry weight, 15 to 80% by dry weight, 20 to 80% by dry weight, 25 to 80% by dry weight, 30 to 80% by dry weight, 30 to 75% by dry weight, 30 to 70% by dry weight, 30 to 65% by dry weight, 30 to 60% by dry weight, 30 to 55% by dry weight, 30 to 50% by dry weight, 40 to 80% by dry weight, 40 to 70% by dry weight, 50 to 80% by dry weight, 50 to 70% by dry weight, 55 to 65% by dry weight, 60 to 65% by dry weight, 60 to 63% by dry weight, or 60 to 62% by dry weight based on the total weight of the liposome preparation, but the present invention is not limited thereto.

In the present invention, the lyso-PC may be included at 0.5 to 10% by dry weight, 0.5 to 8% by dry weight, 0.5 to 7% by dry weight, 0.5 to 6% by dry weight, 0.5 to 5% by dry weight, 0.5 to 4% by dry weight, 1 to 8% by dry weight, 1 to 7% by dry weight, 1 to 6% by dry weight, 1 to 4% by dry weight, 2 to 8% by dry weight, 2 to 7.5% by dry weight, 2 to 6% by dry weight, 2 to 5% by dry weight, 2 to 4% by dry weight, 2.5 to 7.5% by dry weight, 2.5 to 7% by dry weight, 2.5 to 6.5% by dry weight, 3 to 8% by dry weight, 3 to 7% by dry weight, 3 to 6% by dry weight, 3 to 5% by dry weight, 3 to 4% by dry weight, 5 to 10% by dry weight, 5 to 9% by dry weight, 5 to 8% by dry weight, 5 to 7% by dry weight, 5 to 6% by dry weight, or 5 to 5.5% by dry weight based on the total weight of the liposome preparation, but the present invention is not limited thereto.

In the present invention, the liposome membrane of the sonosensitive liposome preparation may be composed of DSPC, DSPE-mPEG2000, DOPE, cholesterol, and lyso-PC, but the present invention is not limited thereto.

The liposome of the present invention is formed by an amphipathic compound including phospholipids. Such an amphipathic compound is typically arranged at an interface between an aqueous medium and an intrinsically insoluble organic solvent to stabilize emulsified solvent microdroplets. The amphipathic compound includes compounds having molecules containing a hydrophilic polar head moiety (e.g., a polar or ionic group) capable of reacting with an aqueous medium and a hydrophobic organic tail moiety (e.g., a hydrocarbon chain) capable of, for example, reacting with an organic solvent. The amphipathic compound is a compound that may stabilize a mixture of materials which may not be generally mixed by other methods, such as a mixture of two immiscible liquids (e.g., water and oil), a mixture of a liquid and a gas (e.g., gas microbubbles in water), or a mixture of a liquid and insoluble particles (e.g., metal nanoparticles in water).

The term "ultrasound" used in the present invention generally refers to sound waves whose frequency is greater than a frequency of 16 Hz to 20 kHz, which corresponds to that of sound waves that humans can hear. High-intensity focused ultrasound may have an instantaneous thermal effect (65-100° C.), a cavitation effect, a mechanical effect, and a sonochemical effect according to the energy and the number of vibrations by introducing focused ultrasound which provides continuous and high-intensity ultrasound energy to a focal point. Ultrasound is not harmful to the human body when passing through the human tissues, but high-intensity ultrasound forming a focal point generates a sufficient amount of energy to cause coagulative necrosis and a thermal ablation effect regardless of the type of tissue.

According to the present invention, the ultrasound refers to sound waves whose frequency is greater than 16 Hz to 20 kHz, which corresponds to a range of an audible frequency. The ultrasound may be high-intensity focused ultrasound (HIFU), high-intensity non-focused ultrasound, or a combination thereof, but the present invention is not limited thereto. The HIFU refers to ultrasound that focuses high-intensity ultrasound energy on one spot to form a focal point. The HIFU may be ultrasound-guided high-intensity focused ultrasound (ultrasound-guided HIFU) and magnetic resonance imaging-guided high-intensity focused ultrasound (Mill-guided HIFU), depending on what high-intensity focused ultrasound treatments are performed while viewing any of certain images. The frequency of the ultrasound may be, for example, in a range of 20 kHz to 3.0 MHz, 40 kHz to 2.0 MHz, 60 kHz to 2.0 MHz, 80 kHz to 2.0 MHz, 100 kHz to 2.0 MHz, 150 kHz to 2.0 MHz, 200 kHz to 2.0 MHz, 250 kHz to 2.0 MHz, 300 kHz to 2.0 MHz, 350 kHz to 2.0 MHz, 400 kHz to 2.0 MHz, 450 kHz to 2.0 MHz, 500 kHz to 2.0 MHz, 550 kHz to 2.0 MHz, 600 kHz to 2.0 MHz, 650 kHz to 2.0 MHz, 700 kHz to 2.0 MHz, 750 kHz to 2.0 MHz, 800 kHz to 2.0 MHz, 850 kHz to 2.0 MHz, 900 kHz to 2.0 MHz, 950 kHz to 2.0 MHz, 600 kHz to 1.5 MHz, 650 kHz to 1.5 MHz, 700 kHz to 1.5 MHz, 750 kHz to 1.5 MHz, 800 kHz to 1.5 MHz, 850 kHz to 1.5 MHz, 900 kHz to 1.5 MHz, 950 kHz to 1.5 MHz, 1 MHz to 1.5 MHz, 600 kHz to 1.3 MHz, 650 kHz to 1.3 MHz, 700 kHz to 1.3 MHz, 750 kHz to 1.3 MHz, 800 kHz to 1.3 MHz, 850 kHz to 1.3 MHz, 900 kHz to 1.3 MHz, 950 kHz to 1.3 MHz, 600 kHz to 1.1 MHz, 650 kHz to 1.1 MHz, 700 kHz to 1.1 MHz, 750 kHz to 1.1 MHz, 800 kHz to 1.1 MHz, 850 kHz to 1.1 MHz, 900 kHz to 1.1 MHz, or 950 kHz to 1.1 MHz, but the present invention is not limited thereto.

The liposome is a sonosensitive liposome. The term "sonosensitive liposome" refers to a liposome whose permeability increases when the liposome is exposed to ultrasound. As a result, when the liposome is exposed to the ultrasound, a drug included in the liposome may be released.

The liposome may have ensured stability. The term "stability" refers to a condition in which a drug encapsulated in a blood liposome is not released in a state in which the liposome is not exposed to ultrasound. According to one specific embodiment, the liposome has a drug release rate of up to 30% or less when a release rate of a drug encapsulated in the liposome is measured for 60 minutes every 20 minutes under vortexing conditions at room temperature (20 to 25° C.) for 60 minutes.

The liposome may have a particle size (for example, a diameter) of 50 nm to 500 nm, 50 nm to 400 nm, 50 nm to 300 nm, 50 nm to 200 nm, 60 nm to 200 nm, 70 nm to 200 nm, 80 nm to 200 nm, 90 nm to 200 nm, 100 nm to 200 nm, 110 nm to 190 nm, 120 nm to 180 nm, 130 nm to 170 nm, 140 nm to 170 nm, 140 nm to 160 nm, or approximately 150 nm. According to one specific embodiment, the liposome may have a particle size 100 nm to 200 nm. Here, a method of measuring the particle size is performed using a method described in Example 1 of this specification, but the present invention is not limited thereto. In this case, the particle size may be measured using other methods known in the art, and may be converted into an equivalent level of value.

Also, the present invention provides a pharmaceutical composition for preventing or treating cancer, which includes the sonosensitive liposome preparation.

Also, the present invention provides composition for drug delivery, which includes the sonosensitive liposome having a drug encapsulated therein as an active ingredient, wherein the liposome includes DSPC, DSPE-mPEG2000, DOPE, and lyso-PC; or includes DSPC, DSPE-mPEG2000, DOPE, cholesterol, and lyso-PC.

The term "drug" used in the present invention refers to any compound having a desired biological activity. The desired biological activity includes activities useful for diagnosing, curing, alleviating, treating, or preventing a disease in humans or other animals.

In the present invention, the drug may be an anticancer drug, and may, for example, include one or more selected from the group consisting of doxorubicin, paclitaxel, docetaxel, cisplatin, Gleevec, 5-fluorouracil (5-FU), tamoxifen, carboplatin, topotecan, belotecan, imatinib, irinotecan, floxuridine, vinorelbine, gemcitabine, leuprolide, flutamide, zoledronate, methotrexate, camptothecin, vincristine, hydroxyurea, streptozotocin, valrubicin, retinoic acid, mechlorethamine, chlorambucil, busulfan, doxifluridine, vinblastine, mitomycin, prednisone, Afinitor, and mitoxantrone, but the present invention is not limited thereto.

According to the present invention, the drug and the sonosensitive liposome may be preferably mixed at a mass ratio (w/w %) of 1:2 to 1:20, more preferably at a mass ratio (w/w %) of 1:2 to 1:20, 1:2 to 1:18, 1:2 to 1:16, 1:2 to 1:14, 1:2 to 1:12, 1:2 to 1:10.5, 1:2.5 to 1:10.5, 1:2.5 to 1:5, 1:2 to 1:4, 1:2.5 to 1:4.5, 1:2.5 to 1:4, 1:2.5 to 1:3, 1:1:5 to 1:10.5, 1:5.5 to 1:10.5, 1:6 to 1:10.5, 1:6.5 to 1:10.5, 1:7 to 1:10.5, 1:7 to 1:10, 1:7 to 1:9, or approximately 1:8, but the mixing ratio of the drug and the sonosensitive liposome is not limited as long as the drug may be effectively encapsulated in the liposome.

According to the present invention, the term "encapsulation efficiency" may be used interchangeably with entrapment efficiency. According to the present invention, the sonosensitive liposome having a drug encapsulated therein may have an anticancer drug encapsulation efficiency of 30% to 100%, 40% to 100%, 50% to 100%, 60% to 100%, 65% to 100%, 70% to 100%, 75% to 100%, 76% to 100%, 77% to 100%, 80% to 100%, 85% to 100%, 87% to 100%, 88% to 100%, 90% to 100%, or 95% to 100%, but the present invention is not limited thereto.

The encapsulation efficiency refers to the entrapment efficiency with respect to an amount of the added drug, but the present invention is not limited thereto. Here, a method of measuring the drug encapsulation efficiency is performed by a method described in Example 1 of this specification, but the present invention is not limited thereto. In this case, the drug encapsulation efficiency may be measured using other methods known in the art, and may be converted into an equivalent level of value.

According to the present invention, the sonosensitive liposome having a drug encapsulated therein may have a drug release rate of 10% to 100%, 50% to 100%, 60% to 100%, 65% to 100%, 70% to 100%, or 75% to 100%, but the present invention is not limited thereto. The drug release rate may refer to a release rate with respect to an amount of the added drug, but the present invention is not limited thereto. Here, a method of measuring the release rate is performed by a method described in Example 2 of this specification, but the present invention is not limited thereto. In this case, the release rate may be measured using other methods known in the art, and may be converted into an equivalent level of value.

According to the present invention, the sonosensitive liposome having a drug encapsulated therein may have a drug release rate 0.1% to 100%, 0.1% to 80%, 0.1% to 60%, 0.1% to 40%, 0.1% to 30%, 0.1% to 20%, or 30% or less in blood when the sonosensitive liposome is not treated with ultrasound, but the present invention is not limited thereto.

In the present invention, the sonosensitive liposome preparation or a pharmaceutical composition including the same may be administered sequentially or concurrently with sonication, but the present invention is not limited thereto.

The term "cancer" used in the present invention generally refers to all types of diseases caused in cells having aggressive characteristics by which the cells divide and grow while ignoring normal growth limitations, invasive characteristics by which the cells penetrate into the surrounding tissues, and metastatic characteristics by which the cells spread to other sites in the body.

According to the present invention, the type of cancer is not particularly limited as long as it is known to be a malignant tumor in the art. For example, the cancer may be selected from the group consisting of breast cancer, colon cancer, lung cancer, small-cell lung cancer, gastric cancer, liver cancer, blood cancer, bone cancer, pancreatic cancer, skin cancer, head or neck cancer, skin or intraocular melanoma, uterine cancer, ovarian cancer, rectal cancer, anal cancer, colorectal cancer, fallopian tube carcinoma, endometrial carcinoma, cervical cancer, vaginal cancer, vulva carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureteral cancer, renal cell carcinoma, renal pelvic carcinoma, CNS tumors, primary CNS lymphoma, spinal cord tumors, brainstem glioma, and pituitary adenoma.

According to the present invention, the term "prevention" refers to all types of actions for suppressing or delaying the onset of cancer by administering the composition according to the present invention.

According to the present invention, the term "treatment" refers to all types of actions for alleviating or benefiting cancer and symptoms thereof by administering the composition according to the present invention.

In the present invention, the term "pharmaceutical composition" refers to a composition that is prepared for the purpose of preventing or treating cancer, and may be formulated into various forms and used using each of conventional methods. For example, the pharmaceutical composition may be formulated into oral formulations such as a powder, granules, a tablet, a capsule, a suspension, an emulsion, a syrup, and the like, and may be formulated into forms such as skin preparations for external use (e.g., a cream, a gel, a patch, a spray, an ointment, a plaster, a lotion, a liniment, a pasta, a cataplasma, and the like), suppositories, and sterile injection solutions.

The pharmaceutical composition according to the present invention may further include a suitable carrier, excipient or diluent typically used for preparing the pharmaceutical composition. In this case, the carrier, excipient and diluent that may be included in the composition may include lactose, dextrose, sucrose, an oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oils.

When formulated, the composition may be prepared using a commonly used diluent or excipient such as a filler, an extender, a binder, a wetting agent, a disintegrant, a surfactant, and the like.

A solid preparation for oral administration may include a tablet, a pill, a powder, granules, a capsule, and the like. Such a solid preparation is prepared by mixing at least one excipient, for example, starch, calcium carbonate, sucrose or lactose, gelatin, and the like with an extract. Also, lubricants such as magnesium stearate, talc, and the like are also used in addition to the simple excipients. A liquid preparation for oral administration may include a suspension, an oral liquid, an emulsion, syrup, and the like. In addition to the commonly used simple diluents such as water, liquid paraffin, and the like, the liquid preparation may include various excipients, for example, a wetting agent, a sweetening agent, a fragrance, a preservative, and the like. A preparation for parenteral administration includes a sterile aqueous solution, a non-aqueous solvent, a suspension, an emulsion, a freeze-dried preparation, a suppository, and the like. Propylene glycol, polyethylene glycol, a vegetable oil (such as olive oil), an injectable ester (such as ethyl oleate), and the like may be used as a non-aqueous solvent and a suspending agent. Witepsol, Macrogol, Tween 61, cacao butter, laurine butter, glycerogelatin, and the like may be used as a base of the suppository.

The pharmaceutical composition of the present invention may be administered orally or administered parenterally (for example, intravenously, subcutaneously, intraperotoneally, or by topical application) according to a desired method, and the dose may depend on the condition and weight of a patient, the severity of a disease, the type of drug, a route of administration, and an administration duration, but may be suitably chosen by those skilled in the art.

The pharmaceutical composition of the present invention is administered at a pharmaceutically effective amount. According to the present invention, the term "pharmaceutically effective amount" refers to an amount sufficient to treat a disease at a reasonable benefit/risk ratio applicable to medical treatment, and a level of an effective dose may be determined according to the type and severity of a patient's disease, the activity of a drug, the sensitivity to the drug, an administration duration, a route of administration and a secretion rate, a treatment period, factors including concurrently used drugs, and other factors well known in the medical field. The pharmaceutical composition according to the present invention may be administered as an individual therapeutic agent or administered in combination with other therapeutic agents. In this case, the pharmaceutical composition may be administered sequentially or simultaneously with conventional therapeutic agents, and may be administered in single or multiple doses. It is important to administer an amount of the pharmaceutical composition that may realize the maximum effect at the minimum amount without any side effects in consideration of all the factors described above. In this case, the amount of the pharmaceutical composition may be easily determined by those skilled in the art. The dose may be administered once a day or administered in equally divided doses.

The pharmaceutical composition for preventing or treating cancer according to the present invention may be used in combination with the liposome included in the composition, and the composition may further include one or more selected from the group consisting of anticancer drugs, image contrast agents, antibiotics, anti-inflammatory agents, proteins, cytokines, peptides, and antibodies in addition to the sonosensitive liposome.

According to the present invention, the term "administration" refers to a process of providing a predetermined amount of the composition of the present invention to a subject using any suitable method.

According to the present invention, the term "subject" refers to a target in need of disease treatment, to which the composition of the present invention may be administered. More specifically, the subject refer to a mammal such as a human or a non-human primate, a mouse, a dog, a cat, a horse, cattle, and the like.

Also, the present invention provides a method of preparing the sonosensitive liposome, which includes one preparation process selected from the group consisting of the following Preparation Processes 1 to 3:

[Preparation Process 1]

(a) dissolving DSPC, DSPE-mPEG2000, DOPE, and lyso-PC in a first organic solvent;

(b) evaporating the organic solvent to prepare a liposome membrane;

(c) hydrating the liposome membrane in an aqueous solution and stirring the liposome membrane solution; and (d) extruding the liposome membrane solution through an extruder.

[Preparation Process 2]

(a) dissolving DSPC, DSPE-mPEG2000, DOPE, and lyso-PC in ethanol;

(b) hydrating the ethanol solution prepared in Step (a) in an aqueous solution and stirring the ethanol solution; and (c) extruding the ethanol solution through an extruder.

[Preparation Process 3]

(a) dissolving DSPC, DSPE-mPEG2000, DOPE, and lyso-PC in a first organic solvent;

(b) mixing the first organic solvent solution prepared in Step (a) and an aqueous solution while changing the flow velocities thereof using a channel of a microfluidic system; and (c) removing the organic solvent.

In the present invention, Preparation Process 2 may further include evaporating ethanol after Step (b), but the present invention is not limited thereto.

In the present invention, the aqueous solution may be an aqueous ammonium sulfate solution, but the present invention is not limited thereto.

In the present invention, the removing of the organic solvent may include evaporating the organic solvent, but the present invention is not limited thereto.

In the present invention, the microfluidic system uses a known high-pressure homogenization method using a high-pressure emulsifying device, but the present invention is not limited thereto. For information on the microfluidic system, Whitesides, G. M. (2006). *The origins and the future of microfluidics. Nature,* 442(7101), 368-373 may be referenced.

In the present invention, the first organic solvent may include one or more selected from the group consisting of dimethylacetamide, dimethylformamide, dimethyl sulfoxide, chloroform, methanol, ethanol, and ether, but the present invention is not limited thereto.

The liposome preparation prepared by the method of the present invention may be used as an injection and may be used for the percutaneous and intranasal delivery of a drug to the lungs. The technology required for such preparation, and the pharmaceutically suitable carriers, additives, and the like are widely known to people having ordinary skill in the field of manufacturing pharmaceuticals, and Remington's Pharmaceutical Sciences (19th ed.,1995) may be referenced.

Also, a temperature required to extrude the liposome may be widely adjusted in a range of room temperature to a phase transition temperature of each material, and the extrusion may be repeatedly performed an appropriate number of times in order to make the size of the liposome uniform.

Also, the sonosensitive liposome may be prepared using a microfluidic process. An organic solvent used in the microfluidic process may, for example, include one or more selected from the group consisting of dimethylacetamide, dimethylformamide, dimethyl sulfoxide, chloroform, methanol, ethanol, and ether. According to one embodiment of the present invention, a liposome is prepared through a microfluidic process using ethanol and an aqueous ammonium sulfate solution in one-channel and two-channel microfluidic systems, respectively.

Also, a concentration of the phospholipids dissolved in the organic solvent in the preparation method may be, for example, in a range of 1 to 300 mg/mL 1 to 200 mg/mL, 1 to 100 mg/mL, 1 to 80 mg/mL, 1 to 70 mg/mL, 1 to 50 mg/mL, 1 to 30 mg/mL, 1 to 20 mg/mL, 1 to 10 mg/mL, 1 to 5 mg/mL, 1 to 3 mg/mL, 3 to 5 mg/mL, or 60 to 70 mg/mL, but the present invention is not limited thereto.

Also, a flow rate of the microfluidic process in the preparation method may be, for example, in a range of 1 to 50 mL/min, 1 to 40 mL/min, 1 to 30 mL/min, 1 to 25 mL/min, 1 to 20 mL/min, or 1 to 15 mL/min, but the present invention is not limited thereto.

According to one embodiment of the present invention, liposomes were prepared with a varying molar ratio of MSPC, and physical properties of the liposomes were then compared. As a result, it was confirmed that the liposome had the highest stability while showing an excellent drug release rate when the liposome was prepared using approximately 5 moles of MSPC (see Examples 2 and 7).

According to another embodiment of the present invention, liposomes were prepared with a varying molar ratio of cholesterol, and physical properties of the liposomes were then compared. As a result, it was confirmed that the cholesterol had a slight effect on sonosensitivity regardless of the ratio of the cholesterol (see Example 3).

According to still another embodiment of the present invention, liposomes optionally including DOPC or DOPE were prepared, and physical properties of the liposomes were then compared. As a result, it was confirmed that DOPE was more suitable for the preparation of the sonosensitive liposome (see Example 4).

According to yet another embodiment of the present invention, liposomes were prepared with a varying molar ratio of DSPC, and physical properties of the liposomes were then compared. As a result, it was confirmed that the release rate of the drug by the ultrasound treatment decreased with an increasing concentration of DSPC (see Example 5).

According to yet another embodiment of the present invention, the release rate of the drug from the liposome of the present invention according to the presence/absence of ultrasound treatment and the elapse of time was determined. As a result, it was confirmed that the drug release rate remarkably increased in the group irradiated with ultrasound compared to the group not irradiated with ultrasound, and that the particle size distribution was maintained without any change (see Example 8).

According to yet another embodiment of the present invention, the cancer cell death effects of the liposome of the present invention and commercially available liposome drugs according to the presence/absence of ultrasound treatment were determined. As a result, it was confirmed that the sonosensitive liposome of the present invention has a superior cancer cell death effect compared to the commercially available liposome drugs (see Example 10).

According to yet another embodiment of the present invention, the breast cancer cell-penetrating effects of the liposome of the present invention and the commercially available liposome drugs according to the presence/absence of ultrasound treatment were determined. As a result, it was confirmed that the sonosensitive liposome of the present invention had a superior cancer cell-penetrating effect compared to the commercially available liposome drugs (see Example 11).

The terms used in the present invention have been selected as widely used general terms as much as possible in consideration of the functions in the present invention, but this may vary according to the intention or precedent of the person skilled in the art, the emergence of new technologies and the like. In addition, in certain cases, there are also terms arbitrarily selected by the applicant, in which case the meaning will be described in detail in the description of the invention. Therefore, the terms used in the present invention should be defined based on the meanings of the terms and the contents throughout the present invention, rather than the names of the simple terms.

Throughout the specification of the present invention, when any certain part is said to "include" any component, this means that it may further include other components, rather than excluding other components unless otherwise stated. In addition, the terms "approximately," "substantially," the like used throughout the specification of the present invention are used at, or in close proximity to, numerical values when manufacturing and material tolerances inherent in the indicated meanings are intended to aid in understanding the present invention. Accurate or absolute figures are used to assist in the prevention of unfair use by unscrupulous infringers.

Throughout the specification of the present invention, the term "combination thereof" included in a Markush type expression refers to a mixture or combination of one or more selected from the group consisting of components described in the Markush type expression, and thus means that the mixture or combination includes one or more selected from the group consisting of the components.

MODE FOR INVENTION

Hereinafter, preferred embodiments of the present invention are presented in order to aid in understanding the present invention. However, it should be understood that the following embodiments are given by way of illustration only to more easily understand the present invention, and are not intended to limit the present invention.

EXAMPLES

Materials listed in the following table were used in examples.

| Materials | IUPAC Name |
|---|---|
| DSPC | 1,2-distearoyl-sn-glycero-3-phosphatidylcholine |
| DSPC-mPGE2000 | 1,2-distearoyl-sn-glycero-3-phosphoethanol amine with conjugated methoxyl poly(ethylene glycol 2000) |
| DOPE | 1,2-dioleoyl-sn-glycero-3-phosphoethanolamine |
| DOPC | 1,2-dioleoyl-sn-glycero-3-phosphatidylcholine |
| Cholesterol | cholesterol |
| Lyso-PC (Types) | 1) 1-stearoyl-2-hydroxy-sn-glycero-3-phosphocholine (18:0)<br>2) 1-oleoyl-2-hydroxy-sn-glycero-3-phosphocholine (18:1)<br>3) 1-heptadecanoyl-2-hydroxy-sn-glycero-3-phosphocholine (17:0)<br>4) 1-(10Z-heptadecenoyl)-2-hydroxy-sn-glycero-3-phosphocholine (17:1)<br>5) 1-palmitoyl-2-hydroxy-sn-glycero-3-phosphocholine (16:0)<br>6) 1-myristoyl-2-hydroxy-sn-glycero-3-phosphocholine (14:0) |

Example 1: Preparation of Liposome Preparation

First, phospholipids including 32.1 mg of DSPC, 57.0 mg of DSPE-mPEG2000, 23.5 mg of cholesterol, 196.6 mg of DOPE, and 10 mg of lyso-PC (1-stearoyl-2-hydroxy-sn-glycero-3-phosphocholine, MSPC) were dissolved in 5 mL of chloroform. A molar ratio of the respective materials was 10:5:15:65:5. The phospholipid solution dissolved in chloroform was completely evaporated at 45° C. using a rotary evaporator to prepare a thin bilayer phospholipid membrane. Then, the phospholipid membrane was hydrated in a 250 mM concentration of an ammonium sulfate solution while stirring at 55° C. The dispersed liposome solution was extruded at a temperature higher than room temperature using an extruder (size extruder mini, Avanti) equipped with a polycarbonate membrane. The extrusion was repeated until the size of the liposome reached a size of approximately 150 nm.

After the liposome was diluted ten-fold, the particle size distribution of the liposome was measured by a dynamic light scattering (DLS) analysis method using Zetasizer Nano ZS (Malvern). The liposome solution whose particle size distribution was adjusted by the extrusion was introduced through a dialysis membrane having a molecular weight cutoff (MWCO) of 15,000 Dalton, and dialyzed for 12 hours in a solution of 10% sucrose and 10 mM L-histidine.

To encapsulate doxorubicin in the liposome, doxorubicin was added to the dialyzed liposome solution, and stirred at 37° C. and 200 to 300 rpm for 2 hours. The liposome and doxorubicin were mixed at a weight ratio of 8:1. After stirring for 2 hours, the non-encapsulated doxorubicin was separated using a size exclusive chromatography (SEC) method. The absorbances of the encapsulated doxorubicin and the non-encapsulated doxorubicin at a wavelength of 480 nm were measured and quantified.

Example 2: Preparation of Liposome According to Ratio of MSPC and Analysis of Drug Release Rate by Ultrasound Liposomes were prepared in the same manner as in Example 1. In this case, the molar ratio of MSPC was adjusted to 5 or 10, and the molar ratios of the other components were fixed as described in Example 1. For the preparation of the liposomes, the liposomes were hydrated by adjusting ammonium sulfate so that the final concentration of the liposomes reached 16 mg/mL, and a preparation process was performed in the same manner as described above. The particle size distribution of each liposome and the doxorubicin encapsulation efficiency were also analyzed in the same manner as in Example 1.

To measure a level of doxorubicin released from the liposome by ultrasound, each liposome having doxorubicin encapsulated therein was put into a chamber of an ultrasound device (UP200s, Hielscher), and ultrasound was applied at 29 kHz and 92 W/cm$^2$ for one minute. The analysis of the release rate of doxorubicin by ultrasound sensitization was performed using the liposome in which 0.1 mg/mL of doxorubicin was loaded based on doxorubicin. The released doxorubicin and the liposome from which doxorubicin was released were separated using a size exclusive chromatography (SEC) method. The quantitative analysis of doxorubicin was performed by measuring the absorbance at 480 nm. Table 1 and FIG. 1 show the compositions and particle size distributions of the respective liposomes, the entrapment efficiency of doxorubicin, and the release rate of doxorubicin by ultrasound.

TABLE 1

Particle size distributions of liposomes by molar ratio of MSPC, entrapment efficiency of doxorubicin, and release rate of doxorubicin by ultrasound

| Sample No. | DSPC | DSPE-PEK2k | Cholesterol | DOPE | MSPC | Particle size Distribution (d. nm) | Entrapment efficiency (%) | Release of DOX (%) |
|---|---|---|---|---|---|---|---|---|
| 1 | 10 | 5 | 15 | 65 | 5 | 162.0 ± 67.7 | 73.1 | 62.3 |
| 2 | | | | | 10 | 116.5 ± 38.9 | 68.0 | 55.7 |

As shown in Table 1 and FIG. 1, the release rate of doxorubicin by the ultrasound sensitization increased as Lyso-PC decreased. From these results, it can be seen that MSPC structurally increased the resistance of the liposome to ultrasound, which served to inhibit the release of a drug. Therefore, the present inventors set the molar ratio of MSPC to 5 to execute the following examples.

Example 3: Analysis of Release Rate of Doxorubicin by Ultrasound Sensitization According to Ratio of Cholesterol To analyze an effect of cholesterol on the release rate of doxorubicin by the ultrasound sensitization of the liposome, liposomes were prepared with a varying molar ratio of cholesterol. A liposome was prepared by changing only the mass of cholesterol, but the molar ratio of DSPC, DSPE-mPEG2000, cholesterol, DOPE, and MSPC was based on 10:5:15:65:5 as described in Example 1. All the prepared liposomes were adjusted to the same concentration of 16 mg/mL, and hydrated using ammonium sulfate (250 mM). The method of preparing a liposome, and methods of analyzing the particle size distribution of the liposome, the entrapment efficiency of doxorubicin, and the release rate of doxorubicin by ultrasound sensitization were performed in the same manner as in Example 1.

Figure 2:
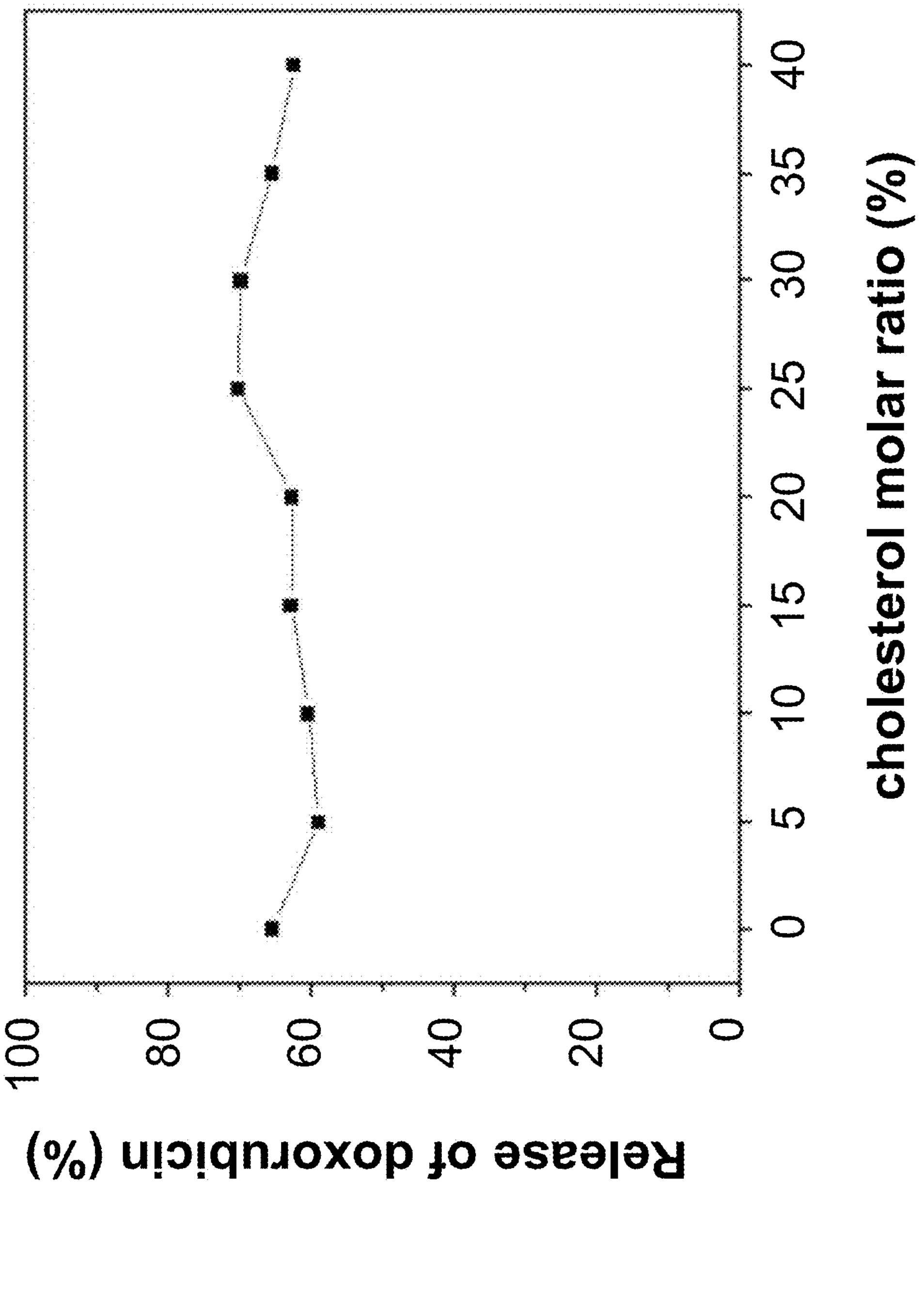
FIG. 2 is a diagram showing a release rate of doxorubicin by the ultrasound sensitization of a liposome according to a change in ratio of cholesterol according to one exemplary embodiment of the present invention.

Table 2 and FIG. 2 show the results of analyzing an effect of cholesterol on the release rate of doxorubicin by ultrasound sensitization.

TABLE 2

Release rate of doxorubicin by ultrasound sensitization of liposome according to change in ratio of cholesterol

| No. | DSPC | DSPE-PEG2k | Cholesterol | DOPE | MSPC | Release of doxorubicin (%, N = 3) |
|---|---|---|---|---|---|---|
| 1 | 10 | 5 | 0 | 65 | 5 | 65.49 |
| 2 | | | 5 | | | 58.97 |
| 3 | | | 10 | | | 60.51 |
| 4 | | | 15 | | | 62.83 |
| 5 | | | 20 | | | 62.80 |
| 6 | | | 25 | | | 70.30 |
| 7 | | | 30 | | | 69.87 |
| 8 | | | 35 | | | 65.49 |
| 9 | | | 40 | | | 62.48 |

As shown in Table 2 and FIG. 2, it was confirmed that, when the ratio of cholesterol was changed from 0 to 40, the ratio of cholesterol in the liposome composition had a slight effect on sonosensitivity, and the liposome had a doxorubicin release rate of 60% or more regardless of the ratio of cholesterol.

Example 4: Comparison of Doxorubicin Release Rate by Ultrasound Sensitization of DOPC and DOPE Liposomes containing DOPC or DOPE at a molar ratio of 65% were prepared in the same manner as in Example 1, and the molar ratios of DSPC, DSPE-mPEG2000, cholesterol, and MSPC were fixed at 10, 5, 15, and 5. The liposomes were hydrated using ammonium sulfate (250 mM) so that the concentration of the liposomes reached 16 mg/mL. Methods of analyzing the particle size distribution, the doxorubicin encapsulation efficiency, and the release rate of doxorubicin by ultrasound sensitization were performed in the same manner as in Example 1.

Figure 3:
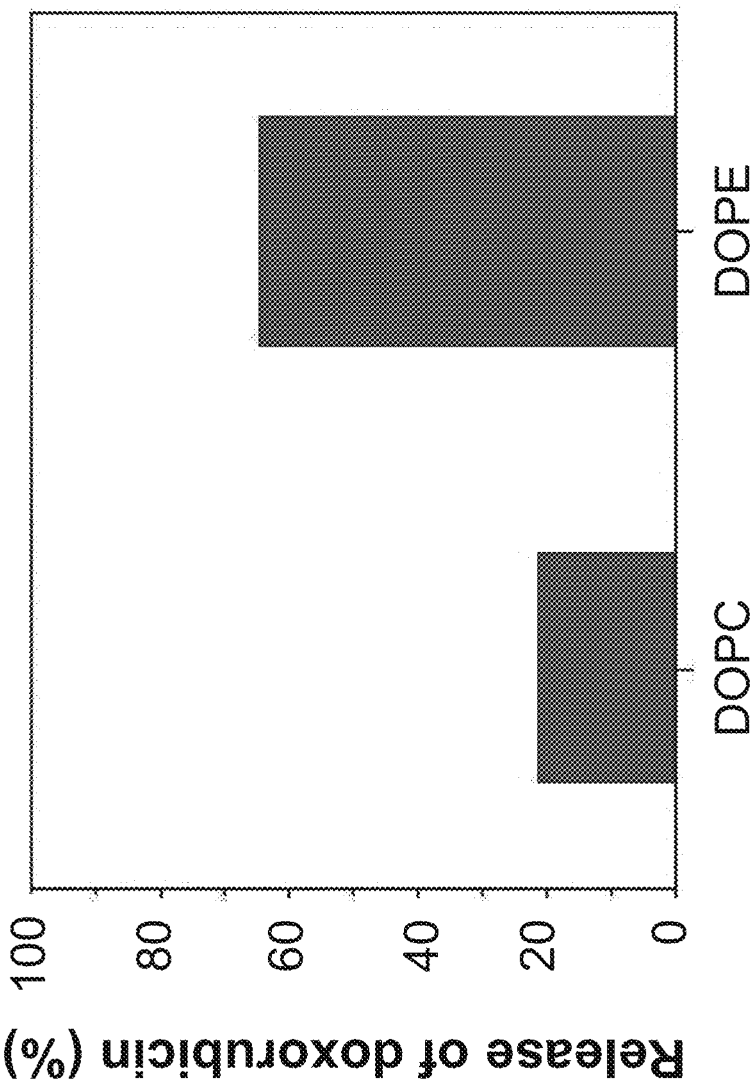
FIG. 3 is a diagram showing a release rate of doxorubicin by the ultrasound sensitization of each of liposomes including DOPC and DOPE, respectively, according to one exemplary embodiment of the present invention.

Table 3 and FIG. 3 show the particle size distribution of each of the liposomes containing DOPC and DOPE, the drug entrapment efficiency, and the release rate of doxorubicin by ultrasound sensitization.

TABLE 3

Particle size distribution of each of liposomes containing DOPC and DOPE, drug entrapment efficiency, and release rate of doxorubicin by ultrasound sensitization

| Sample No. | DSPC | DSPE-PEG2k | Cholesterol | DOPE | DOPC | MSPC | Size distribution (d. nm) | Entrapment efficiency (%) | DOX release (%) |
|---|---|---|---|---|---|---|---|---|---|
| 1 | 10 | 5 | 15 | 65 | — | 5 | 181.8 ± 84.6 | 86.6 | 64.5 |

TABLE 3-continued

Particle size distribution of each of liposomes containing DOPC and DOPE, drug entrapment efficiency, and release rate of doxorubicin by ultrasound sensitization

| Sample No. | DSPC | DSPE-PEG2k | Cholesterol | DOPE | DOPC | MSPC | Size distribution (d. nm) | Entrapment efficiency (%) | DOX release (%) |
|---|---|---|---|---|---|---|---|---|---|
| 2 | | | | — | 65 | | 137.0 ± 67.7 | 82.5 | 21.5 |

As shown in Table 3 and FIG. 3, it was confirmed that significant differences in the particle size distribution and the encapsulation efficiency of doxorubicin were not observed in each of the liposomes containing DOPC and DOPE. However, for the ultrasound-mediated doxorubicin release rate, the liposomes containing DOPE had a release rate of 60% or more, but the liposomes containing DOPC were poorly sensitized by ultrasound, and thus had a release rate of approximately 20%. Accordingly, it was confirmed that DOPE was more suitable than DOPC as the component of the liposome according to the present invention.

Example 5: Analysis of Release of Doxorubicin by Ultrasound Sensitization of Liposome According to Molar Ratio of DSPC Liposomes were prepared by fixing the molar ratios of DSPE-mPEG2000, cholesterol, DOPE, and MSPC at 5%, 15%, 65%, and 5% and increasing the molar ratio of DSPC two- and four-fold based on the 10% DSPC prepared in Example 1. Then, the release rates of doxorubicin by the ultrasound sensitization were compared and analyzed.

The prepared liposomes were hydrated using ammonium sulfate (250 mM) so that the concentration of the liposomes reached 16 mg/mL. Methods of preparing and analyzing the liposomes, and the analysis of the drug release rate by ultrasound sensitization were performed in the same manner as in Examples 1 and 2.

Figure 4:
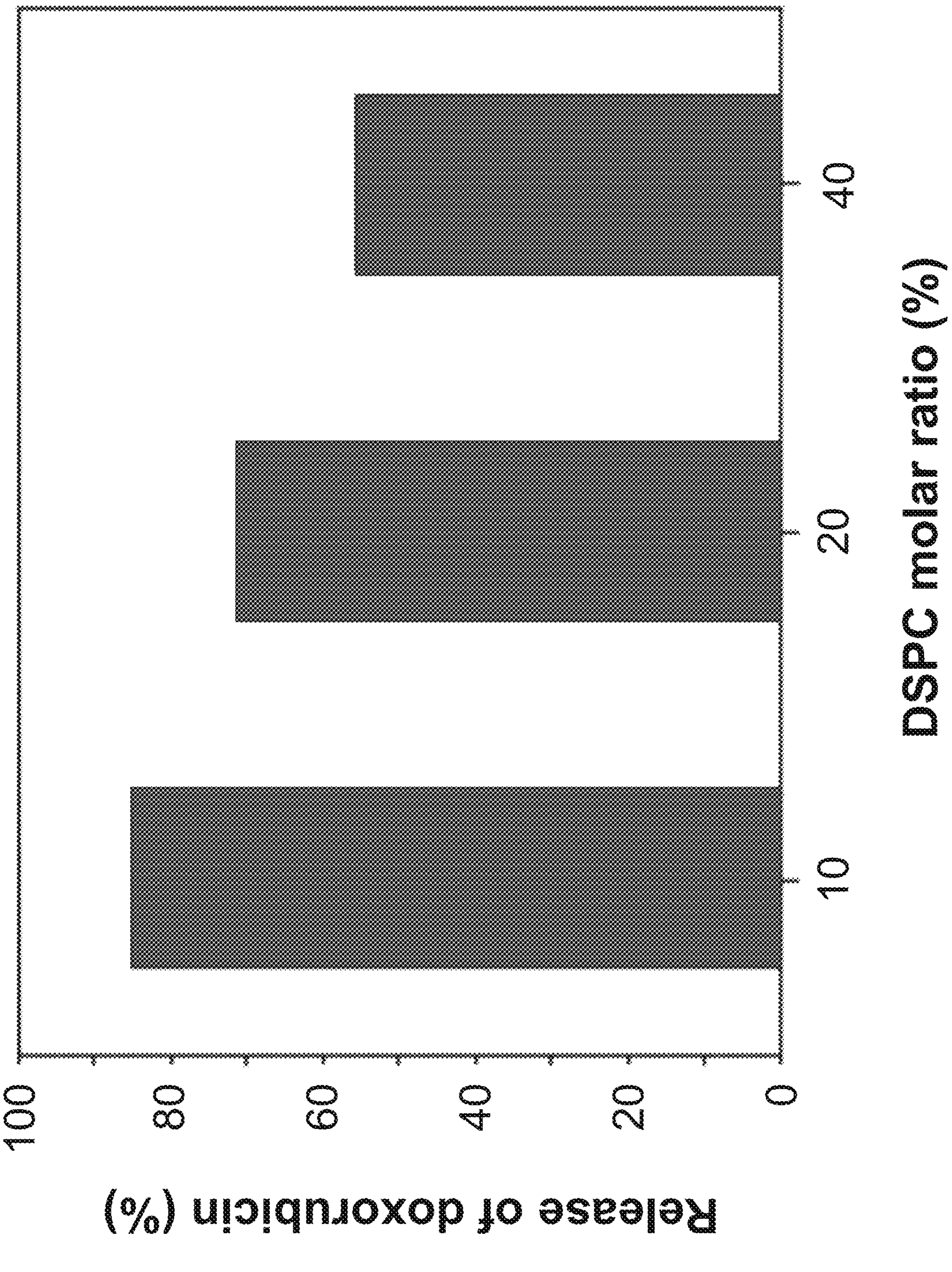
FIG. 4 is a diagram showing a release rate of doxorubicin by the ultrasound sensitization of each liposome according to the ratio of DSPC according to one exemplary embodiment of the present invention.

Table 4 and FIG. 4 show the particle size distribution of each of the liposomes according to the ratio of DSPC, the entrapment efficiency of doxorubicin, and the release rate of doxorubicin in each of the liposomes by ultrasound sensitization.

As shown in Table 4 and FIG. 4, it was confirmed that there were no significant changes in the particle size distribution and the doxorubicin encapsulation efficiency regardless of the change in the ratio of DSPC, and the liposomes had a particle size distribution of approximately 100 nm to 200 nm and a doxorubicin encapsulation efficiency of approximately 75% to 85%.

On the other hand, the release trend of doxorubicin by ultrasound sensitization was compared with an amount of the added DSPC. As a result, it was confirmed that the release rate of doxorubicin by ultrasound decreased with an increasing ratio of DSPC.

Accordingly, it was confirmed that a lower molar ratio of DSPC was more suitable for the preparation of the sonosensitive liposome.

Example 6: Analysis Experiment of Release Rate of Doxorubicin According to Change in Molar Ratio of Liposome Compositions To analyze the release rate of doxorubicin by ultrasound sensitization for compositions constituting a liposome, liposomes were prepared using the composition ratios listed in Table 5. A method of preparing the liposome was performed in the same manner as in Example 1, and the concentration of the liposomes was adjusted to 16 mg/mL using ammonium sulfate (250 mM). Thereafter, a method of entrapping doxorubicin, the entrapment efficiency of doxorubicin, and the release rate of doxorubicin by ultrasound sensitization were also analyzed in the same manner as in Example 1.

TABLE 4

Particle size distribution of each liposome according to molar ratio of DSPC, entrapment efficiency of doxorubicin, and release rate of doxorubicin in each liposome by ultrasound sensitization

| Sample | DSPC | DSPE-PEG2k | Cholesterol | DOPE | MSPC | Size distribution (d. nm) | Entrapment efficiency (%) | Doxorubicin release (%) |
|---|---|---|---|---|---|---|---|---|
| 1 | 10 | 5 | 15 | 65 | 5 | 177.7 ± 98.8 | 83.9 | 84.9 |
| 2 | 20 | | | | | 153.2 ± 68.2 | 75.8 | 71.0 |
| 3 | 40 | | | | | 143.9 ± 84.3 | 81.5 | 55.7 |

TABLE 5

| Analysis results of release rate of doxorubicin by ultrasound sensitization according to change in molar ratio in liposome compositions | | | | | | |
|---|---|---|---|---|---|---|
| Sample No. | DSPC | DSPE-mPEG2k | Cholesterol | DOPE | MSPC | Release of DOX (%) |
| 1 | 23.75 | 5 | 13.75 | 55 | 2.5 | 76.26 |
| 2 | 10 | | 5 | 70 | 10 | 73.82 |
| 3 | 10 | | 15 | 65 | 5 | 69.28 |
| 4 | 27.5 | | 22.5 | 40 | 5 | 67.40 |
| 5 | 31.25 | | 31.25 | 25 | 7.5 | 61.70 |
| 6 | 5 | | 40 | 40 | 10 | 59.25 |
| 7 | 50 | | 25 | 10 | 10 | 51.71 |
| 8 | 50 | | 15 | 20 | 10 | 48.25 |

As shown in Table 5, it was confirmed that the release rate of doxorubicin by ultrasound sensitization tended to increase with an increasing ratio of DOPE, and the cholesterol and MSPC improved the stability of the liposome to inhibit the release of doxorubicin.

Example 7: Evaluation of Stability of Liposome According to Ratio of MSPC

Effects of MSPC on the stability of the liposome according to the inclusion of MSPC and the molar ratio of MSPC included in the liposome were evaluated. Compositions of the liposome used for stability evaluation are as described in Table 6. Liposomes were prepared in the same manner as in Example 1, and a target concentration of doxorubicin in the liposome solution was 0.40 mg per 1.0 mL of the solution.

TABLE 6

| Compositions of liposome used for stability evaluation | | | | | |
|---|---|---|---|---|---|
| Batch No. | DSPC (mol %) | DSPE-PEG2k (mol %) | Cholesterol (mol %) | DOPE (mol %) | MSPC (mol %) |
| 1 | 10 | 5 | 15 | 65 | 0 |
| 2 | | | | | 1 |
| 3 | | | | | 3 |
| 4 | | | | | 5 |
| 5 | | | | | 7 |

To evaluate the stability of the liposome, each of the prepared liposomes was mixed with fetal bovine serum (FBS) at a volume ratio of 1:3, and then stirred.

Figure 5:
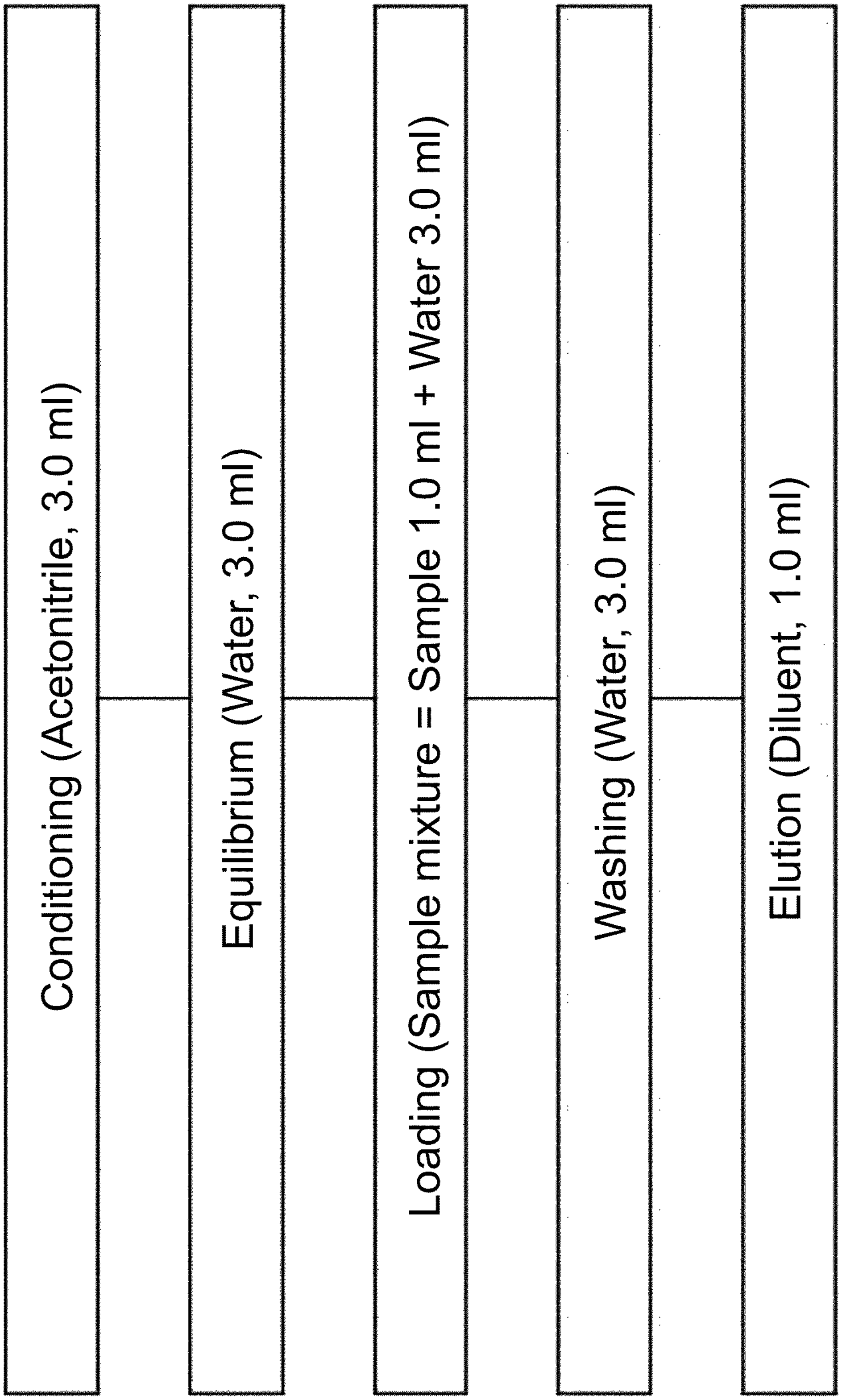
FIG. 5 is a diagram showing a pretreatment process for evaluating 75% serum stability of the liposome according to one exemplary embodiment of the present invention.

The conditions for evaluating the stability of the liposome are as follows: the mixed solution prepared thus was vortexed at room temperature (20 to 25° C.) for 60 minutes. In this case, a portion of the solution was taken every 20 minutes, and an amount of doxorubicin released from the liposome was then measured using a solid phase extraction method (Waters Oasis HLB 3CC). A pretreatment method is as shown in FIG. 5. An elution solution was collected, and analyzed according to the liquid chromatographic analysis conditions shown in Table 7, and an amount of the released doxorubicin was then analyzed.

TABLE 7

| Liquid chromatographic analysis conditions | |
|---|---|
| Mobile Phase | 0.1% TFA in 30% Acetonitrile |
| Flow Rate | 0.2 mL/min |
| Detector | UV (at 254 nm) |
| Injection Volume | 1.0 μL |
| Temperature | 40° C. |
| Run Time | 10 min |
| HPLC Column | Agilent Infinity Lab Poroshell 120 EC-C18 (3.0 × 50 mm, 2.7 μm) |

Figure 6:
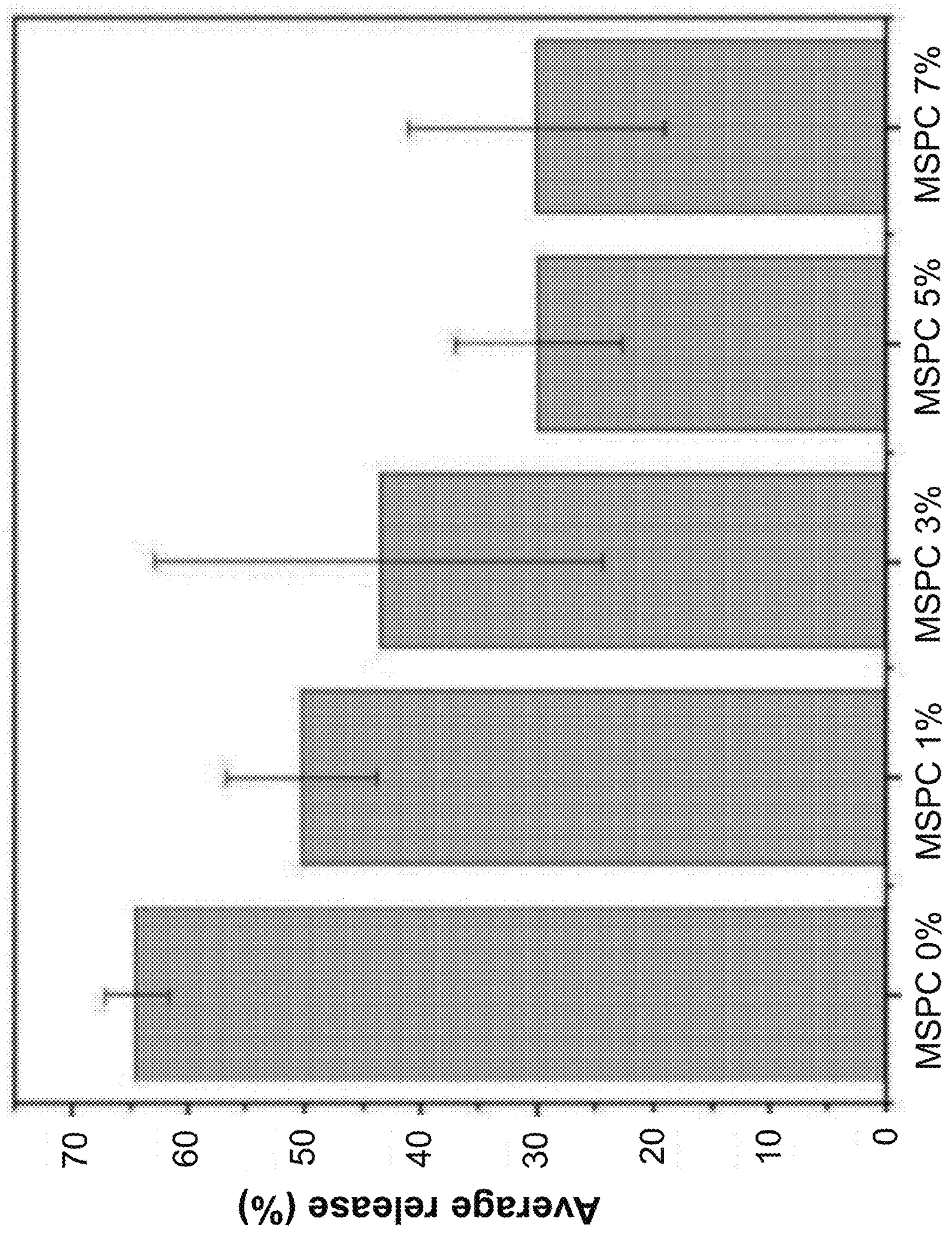
FIG. 6 is a diagram showing an average release rate of doxorubicin according to the ratio of MSPC, showing that the release rate of doxorubicin according to the ratio of MSPC is analyzed in a 75% serum stability evaluation test according to one exemplary embodiment of the present invention.

As shown in FIG. 6, it was confirmed that up to 30% or less of doxorubicin was released because the stability of the liposome was enhanced with an increasing molar ratio of MSPC in the liposome compositions to inhibit the release of the encapsulated doxorubicin. Also, it was confirmed that the liposome was very stable when MSPC was present at a concentration of 5 mol % or more.

Therefore, it was confirmed that liposomes having excellent stability were prepared when the liposomes included MSPC, and the most stable liposomes were prepared when the liposomes included 5 mol % MSPC.

Example 8: Experiment of Release of Doxorubicin from Sonosensitive Liposome Over Time The release rates of doxorubicin over time were analyzed using the liposomes prepared in Example 1. In addition, to compare and evaluate the release trend of a drug by ultrasound sensitization, each of the experimental group (US+) irradiated with ultrasound and the experimental group (US−) not irradiated with ultrasound was sampled at intervals of one hour, and the released doxorubicin and doxorubicin in the liposome were quantitatively analyzed. The release test was performed under the conditions of 37° C. and 150 rpm. The ultrasound-induced release was performed by taking samples at each time points, and the release test solutions were irradiated with ultrasound at a frequency of 29 kHz and an intensity of 92 W/cm$^2$ for one minute. The sampling and ultrasound irradiation were repeated every hour. The released doxorubicin and the liposome were separated in the same manner as in Example 2 using a size exclusive chromatography (SEC) method. The encapsulated doxorubicin and the non-encapsulated doxorubicin was quantified by measuring the absorbance at a wavelength of 480 nm.

Figure 7:
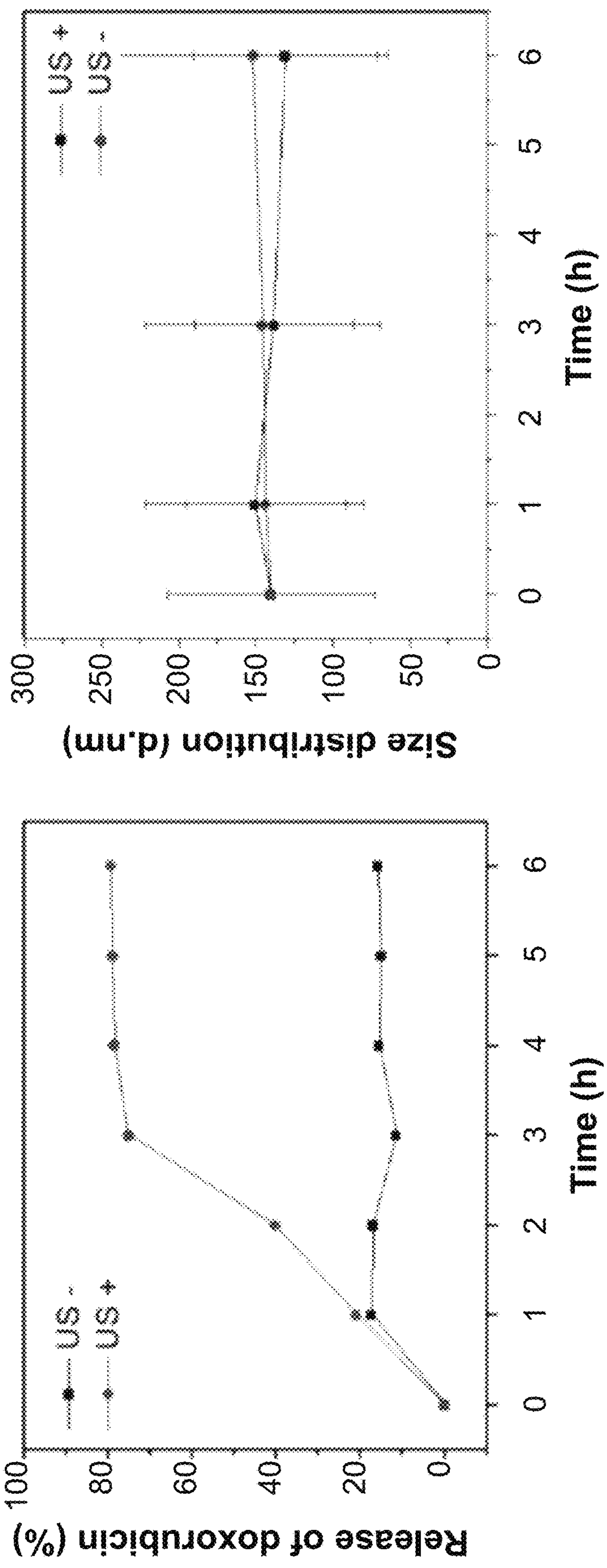
FIG. 7 is a diagram showing the results of comparative evaluation of the release rate of doxorubicin (left) and trend analysis of change in particle size (right) over time and with/without irradiation with ultrasound according to one exemplary embodiment of the present invention.
Figure 8:
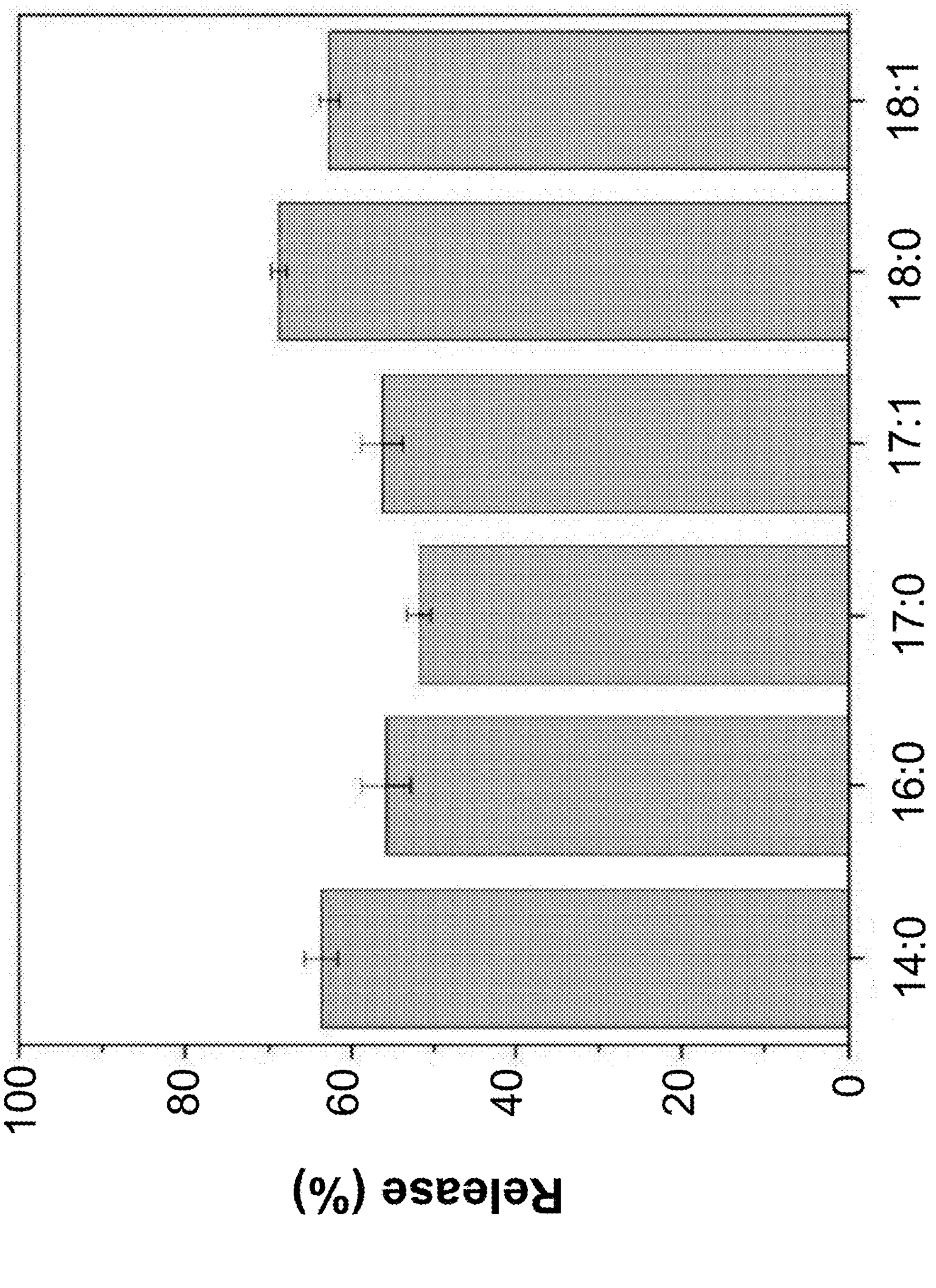
FIG. 8 is a diagram showing drug release rates of sonosensitive liposomes including various types of lyso-PC (14:0, 16:0, 17:0, 17:1, 18:0, 18:1) according to one exemplary embodiment of the present invention.

Table 8 shows the compositions, particle size distribution, and encapsulation efficiency of the liposomes used in this example. Also, Table 9 and FIG. 7 show the trend of comparison and evaluation of the release rate of doxorubicin over time for the sonosensitive liposome and the release rate of doxorubicin according to the ultrasound irradiation.

TABLE 8

| Compositions, particle size distribution and encapsulation efficiency of sonosensitive liposomes | | | | | | | |
|---|---|---|---|---|---|---|---|
| Sample | DSPC | DSPE-PEK2k | Cholesterol | DOPE | MSPC | Size Distribution (d. nm) | Encapsulation efficiency (%) |
| 1 | 10 | 5 | 15 | 65 | 5 | 140.0 ± 67.3 | 79.2 |

TABLE 9

| Comparison and evaluation of release rate of doxorubicin according to treatment of sonosensitive liposome with ultrasound or over time (ultrasound-induced release time: released for one minute every hour) | | | | | | | |
|---|---|---|---|---|---|---|---|
| | | Time (hr) | | | | | |
| | | 1 | 2 | 3 | 4 | 5 | 6 |
| Released DOX | | % | | | | | |
| Ultrasound | US+ | 21.02 | 40.34 | 75.28 | 78.60 | 78.94 | 79.40 |
| irraditaion | US− | 17.42 | 16.99 | 11.52 | 15.53 | 15.18 | 15.87 |

As shown in Table 9 and FIG. 7, the drug release trend of the sonosensitive liposome was compared to the experimental group not irradiated with ultrasound, and the sonosensitive liposome had an improved release rate of approximately 20% when the sonosensitive liposome was irradiated with ultrasound for one minute every hour. On the other hand, the sonosensitive liposome had an initial doxorubicin release rate of approximately 15% in the experimental group not irradiated with ultrasound, and did not further show a doxorubicin release pattern. The sonosensitive liposome had a drug release behavior of approximately 75% for 3 hours (a total of 3 times; irradiated for one minute every hour) through the ultrasound-induced release, and a doxorubicin release rate of approximately 80% for 6 hours (a total of 6 times; irradiated for one minute every hour). Also, the particle size distributions before and after the ultrasound-induced release were analyzed. As a result, it was confirmed that the particle size distributions were maintained without any change, indicating that the pulverization of particles due to an effect of ultrasound did not occur.

Example 9: Preparation of Sonosensitive Liposomes According to Type of Lyso PC and Analysis of Sonosensitivity Results To analyze changes in physical properties and sonosensitivity of the sonosensitive liposome according to the type of Lyso-PC, sonosensitive liposomes was prepared for each type of Lyso-PC.

Five types of Lyso-PCs were selected and tested based on the type of a hydrophobic chain. The types of the selected lyso-PC and the ratios of the components are as shown in Table 10 below.

TABLE 10

| Types of Lyso-PC and component ratios of sonosensitive liposome | | |
|---|---|---|
| Lyso-PC | Acyl chain | Name |
| 1 | 18:0 | 1-stearoyl-2-hydroxy-sn-glycero-3-phosphocholine |
| 2 | 18:1 | 1-oleoyl-2-hydroxy-sn-glycero-3-phosphocholine |
| 3 | 17:0 | 1-heptadecanoy1-2-hydroxy-sn-glycero-3-phosphocholine |
| 4 | 17:1 | 1-(10Z-heptadecenoyl)-2-hydroxy-sn-glycero-3-phosphocholine |
| 5 | 16:0 | 1-palmitoyl-2-hydroxy-sn-glycero-3-phosphocholine |
| 6 | 14:0 | 1-myristoyl-2-hydroxy-sn-glycero-3-phosphocholine |

| Composition of sonosensitive liposome | | | | | |
|---|---|---|---|---|---|
| | DSPC | DSPE-mPEG2k | Cholesterol | DOPE | Lyso-PC |
| Molar ratio (%) | 10 | 5 | 30 | 65 | 5 |
| Content (mg/mL) | 2.99 | 5.31 | 4.39 | 18.31 | 0.99 |

To prepare the sonosensitive liposomes based on the type of the acyl chain of Lyso-PC, volumes of lipids as specified in Table 10 were weighed, and dissolved in 256 mg/mL of ethanol at 60° C. Then, the lipids were added to a 250 mM ammonium sulfate solution, and stirred at 60° C. for an hour to prepare liposomes. In this case, a concentration of the lipid was 32 mg/mL. To reduce the size of the liposome, the liposome was extruded using a high-temperature extruder. The size of the liposome was reduced step by step by passing the liposome through polycarbonate filters of the extruder from a 0.8-μm pore size to a 0.4-μm or 0.2-μm pore size, and this process was repeated until the size of the liposome reached 100 nm to 200 nm. A mixed solution of 10% sucrose and 10 mM histidine used as a solvent for a liposome solution was replaced with ammonium sulfate using a PD-10 column.

Next, to encapsulate doxorubicin, doxorubicin and the liposome were mixed at a mass ratio of 1:8, and then stirred at 37° C. for an hour. The non-encapsulated doxorubicin was separated using a PD-10 column. The size distribution of each of the prepared sonosensitive liposomes and the quantitative amount of doxorubicin were analyzed in the same manner as in Examples 1 and 2.

TABLE 11

| Doxorubicin release rate of sonosensitive liposome according to type of Lyso-PC | | | | | | |
|---|---|---|---|---|---|---|
| Compositions | 14:0 | 16:0 | 17:0 | 17:1 | 18:0 | 18:1 |
| Doxorubicin release (%) | 63.6 ± 1.95 | 55.8 ± 2.89 | 51.8 ± 1.49 | 56.3 ± 2.46 | 68.7 ± 0.89 | 62.6 ± 11.1 |

As shown in Table 11, the doxorubicin release rate according to the types of Lyso-PC had a similar trend with 55% to 65%. Therefore, it was judged that a change in a tail moiety of Lyso-PC did not affect the release rate of doxorubicin by sonosensitivity.

Example 10: Comparison and Analysis of Cancer Cell Death Effect of Sonosensitive Liposome To compare and analyze a cell death effect of the sonosensitive liposome according to the presence/absence of ultrasound irradiation, cancer cell death effects were compared and analyzed according to the presence/absence of ultrasound irradiation using the sonosensitive liposomes of Example 1. An MDA-MB-231 cell line which is a triple-negative breast cancer cell line was used as cancer cells. The MDA-MB-231 cell line was seeded in each well of a 96-well plate at a concentration of 10,000 cells/mL, and then cultured overnight. The cell culture was cultured in a culture broth containing 10% fetal bovine serum (FBS) and 1% antibiotic in Dulbecco's Modified Eagle Medium (DMEM). The culture broth was removed from the wells in which the cells were cultured overnight, and replaced with FBS-free DMEM, and then cultured for an hour. Then, the sonosensitive liposome were added thereto, and cultured for 3 hours. To compare and analyze the cancer cell death according to the ultrasound irradiation, each of the designated wells was treated with a sonosensitive liposome (Sono liposome (US+)) irradiated with ultrasound and a sonosensitive liposome (Sono liposome (US−)) not irradiated with ultrasound. Each of the wells was treated with a 2, 4, 6, 8, or 10 μg/mL concentration of doxorubicin. Caelyx (liposomal doxorubicin HCl), which is a commercially available doxorubicin liposome drug, was used as the control, and each well was treated with Caelyx in the same manner as the sonosensitive liposome. After the wells were treated with each of the liposomes, the wells were cultured for 3 hours, the treated sample present in each well was removed, and the wells were then washed three times with PBS. Then, DMEM containing 10% FBS and 1% antibiotic was again added thereto, and the cells were cultured. After the cells were cultured for 72 hours, the culture broth present in each well was removed, and 20 μL of a MTT reagent having a concentration of 2 mg/mL was added and cultured for 3 hours. The cancer cell death effects were compared and analyzed by adding 200 μL of DMSO to formed formazan in each well and measuring the absorbance at a wavelength of 540 nm using an ELISA reader.

Figure 9:
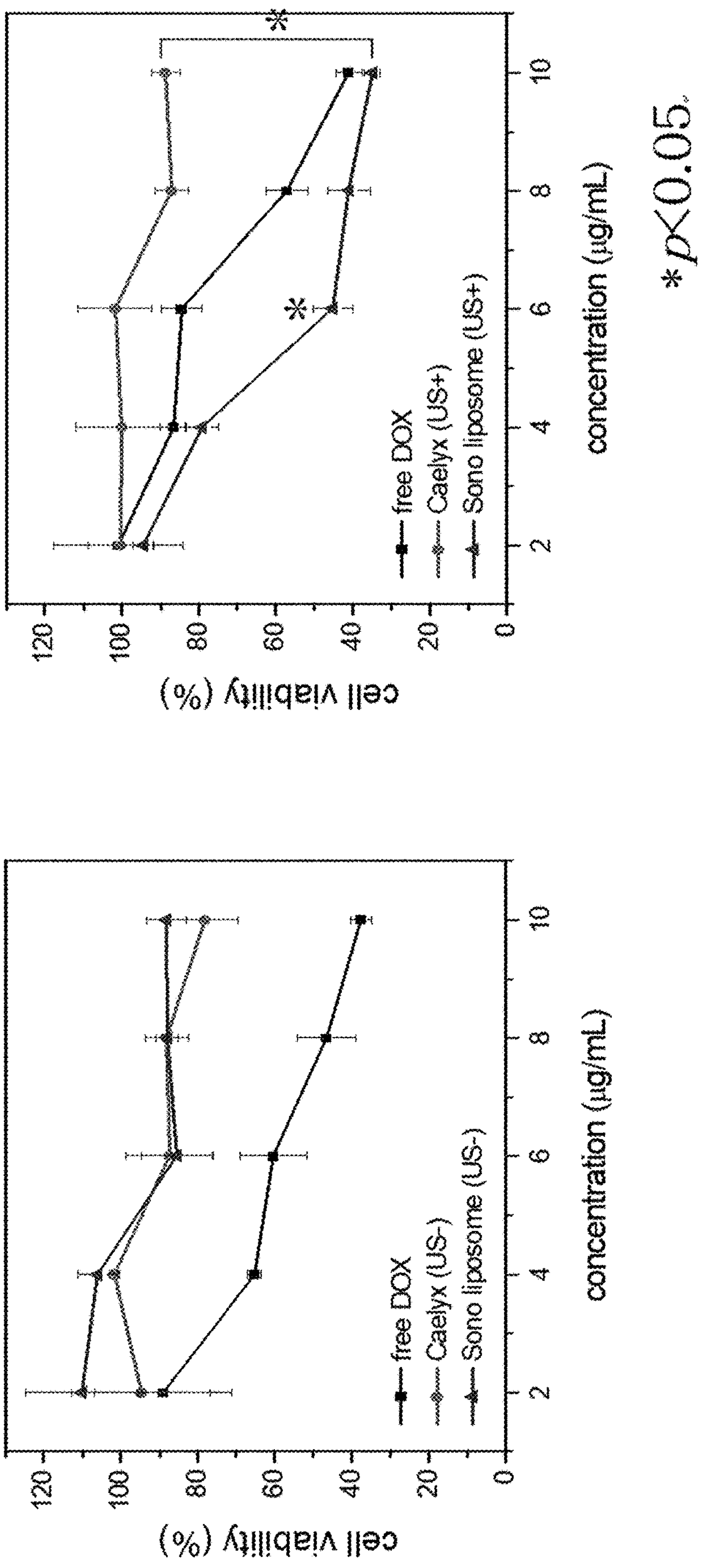
FIG. 9 is a diagram showing a cancer cell death effect with/without irradiation of the sonosensitive liposome according to one exemplary embodiment of the present invention and the control Caelyx with ultrasound.

As a result, as shown in FIG. 9, both of the sonosensitive liposome and Caelyx® had a poor cell death effect on cancer cells in the case of the experimental group not irradiated with ultrasound. Only the doxorubicin had a cancer cell death effect because it penetrated into the cells.

On the other hand, in the case of the experimental group irradiated with ultrasound, Caelyx® had a cancer cell death effect similar to the experimental group not irradiated with ultrasound, whereas the sonosensitive liposome of the present invention had an increasing cancer cell death effect as the encapsulated doxorubicin was released, indicating that drug release was effectively induced by ultrasound. Therefore, it was confirmed the liposome of the present invention shows excellent sensitivity to ultrasound compared to the existing commercially available liposome drugs.

Example 11: Analysis of Cell-Penetrating Effect of Sonosensitive Liposome

To analyze a cell-penetrating effect of the sonosensitive liposome, the cell-penetrating effects of the sonosensitive liposomes of Example 1 were compared with that of Caelyx® and analyzed. A MDA-MB-231 cell line was seeded in an 8-well cell culture chamber at a concentration of 30,000 cells/mL, and cultured overnight. The cell culture broth of Example 9 was used. After the cells were cultured overnight, the cell culture broth present in each well was removed, and the cells were cultured for an hour in a FBS-free culture broth. Thereafter, the sonosensitive liposome and Caelyx® were added to each well according to the ultrasound irradiation. After the cells treated with each of the liposomes, all the treated liposomes were removed after 3 hours, and the cells were washed three times with PBS, and then fixed in 4% paraformaldehyde for 3 minutes. Then, the cell nuclei were stained with 0.01 mg/mL of a DAPI solution, and a mounting solution was added thereto, and covered with a cover glass. To obtain a fluorescent image, a laser having a wavelength of 408 nm for DAPI and a wavelength of 488 nm for doxorubicin were used, and fluorescent images were photographed using a confocal fluorescence microscope. The blue color in the image represents the cell nucleus partially stained with DAPI, and the red color in the image represents the fluorescence of doxorubicin.

Figure 10:
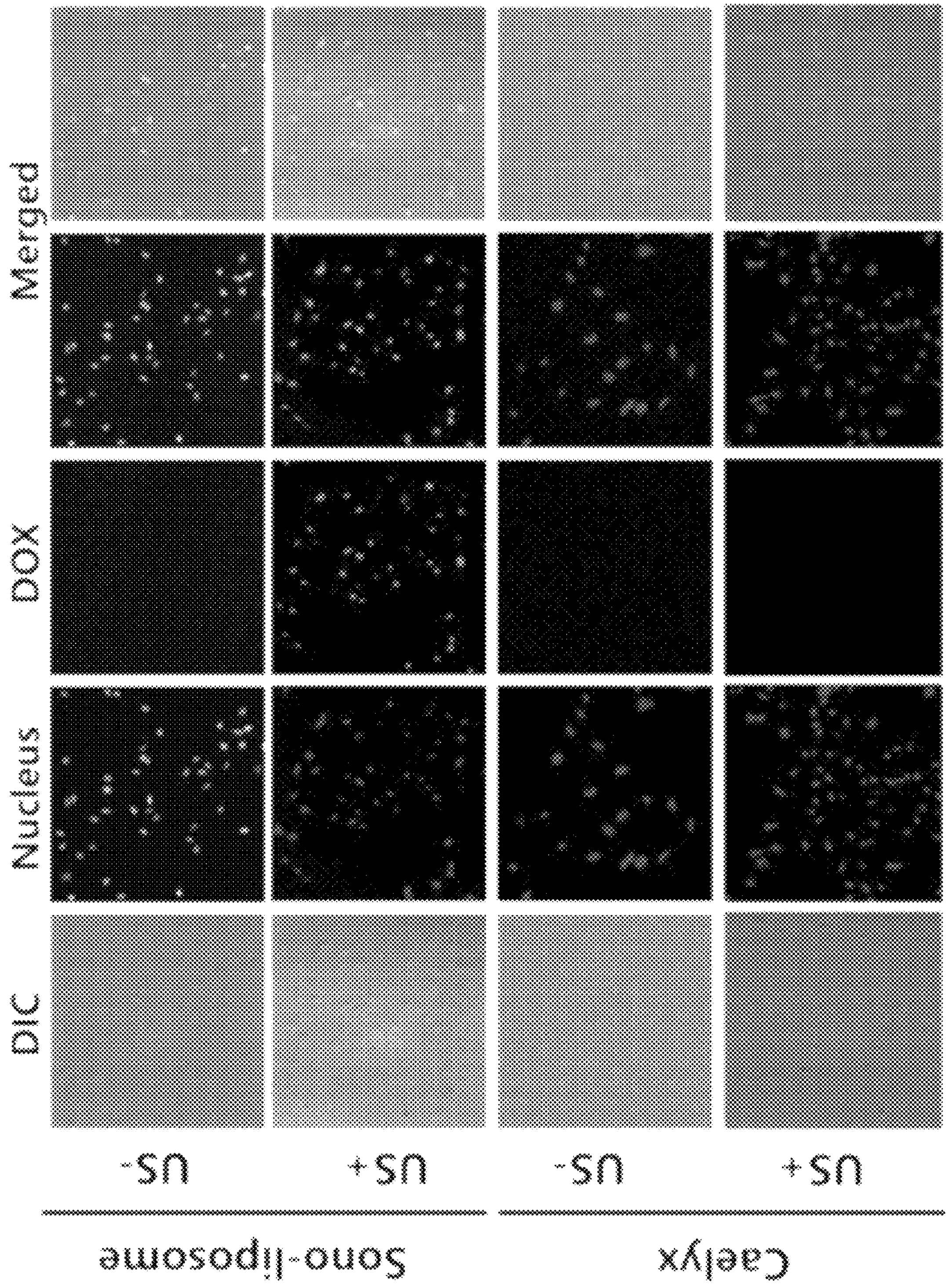
FIG. 10 is a diagram showing a cell-penetrating effect of doxorubicin through the irradiation of the sonosensitive liposome according to one exemplary embodiment of the present invention and the control Caelyx with ultrasound.

As a result, as shown in FIG. 10, both of Caelyx® and the liposome not irradiated with ultrasound did not penetrate into the cells. However, in the case of the experimental group irradiated with ultrasound, doxorubicin was released from the sonosensitive liposome and penetrated into the cells, indicating that excellent sonosensitivity. Also, it was confirmed that doxorubicin penetrated into the cells within 3 hours.

Example 12: Preparation and Evaluation of Sonosensitive Liposome Using Microfluidic Process, and Ultrasound Sensitization Expreiment To prepare a sonosensitive liposome using a microfluidic process, phospholipid components including DSPC, DSPE-mPEG2000, cholesterol, DOPE, and MSPC at a molar ratio of 10, 5, 15, 65, and 5 were dissolved in ethanol. For complete dissolution, the phospholipid components were stored at 75° C. for 10 minutes in an oven so that the phospholipid components were dissolved into a clear solution. The solution was prepared at concentrations of 2, 4, 8, 16, and 64 mg/mL depending on the experimental group.

The microfluidic process is composed of two channels, one channel is a path through phospholipids dissolved in ethanol is administered, and the other channel is a path through 250 mM ammonium sulfate is administered.

For the administration ratio in each channel, an experiment as described in Table 12 was performed, and the total flow rate was adjusted to 3, 12, and 21 mL/min in the case of the experimental group. The liposome solution discharged through the channel was dialyzed for 24 hours through an osmotic membrane having a molecular weight cutoff (MWCO) of 15,000 Da. In this case, the solution was dialyzed in a solution containing 10% sucrose and 10 mM L-histidine. After the dialysis process, a method of analyzing a particle size was performed in the same manner as in in Example 1. Table 12 lists the molar ratios of phospholipid components of the liposome and the experimental conditions.

TABLE 12

Preparative compositions of liposome using microfluidic process, experimental conditions, and particle size distribution

| No. | DSPC | DSPE-PEG2k | Cholesterol | DOPE | MSPC | Volume ratio (ammonium sulfate: ethanol) | Concentration of lipid (mg/mL) | Total flow rate (mL/min) | Size distribution (d. nm) |
|---|---|---|---|---|---|---|---|---|---|
| 1 | 10 | 5 | 15 | 65 | 5 | 3:1 | 4 | 12 | 146.3 ± 54.2 |
| 2 | | | | | | | 2 | | 101.5 ± 28.5 |
| 3 | | | | | | | 8 | | 196.9 ± 95.7 |
| 4 | | | | | | | 16 | | 1,107.0 ± 397.8 |
| 5 | | | | | | 1:1 | 64 | 3 | 118.8 ± 37.3 |
| 6 | | | | | | 1:2 | | | 149.5 ± 76.1 |
| 7 | | | | | | 1:3 | | | 103.9 ± 52.7 |
| 8 | | | | | | 1:2 | | 21 | 60.59 23.8 |
| 9 | | | | | | | | 12 | 42.7 ± 13.9 |

As shown in Table 12, it was confirmed that most of the liposomes had a particle size distribution of 100 to 200 nm. It was confirmed that factors regulating the size of the liposome include a concentration of phospholipids dissolved in ethanol, the total flow rate, and the volume ratio of ethanol and ammonium sulfate. The particle size distribution tended to become smaller with an increasing difference in the volume ratio. Also, the particle size distribution tended to decrease with a faster total flow rate and a lower concentration of phospholipids.

Example 13: Preparation of Liposome by Ethanol Addition Method

Sonosensitive liposomes were prepared by an ethanol addition method using the lipid compositions listed in Table 13 to prepare the sonosensitive liposomes. Each of the lipid mixtures weighed at the molar ratios listed in Table 13 was dissolved in ethanol at 70° C. and a concentration of 256 mg/mL. The lipid solution dissolved into a completely clear solution was mixed with an aqueous 250 mM ammonium sulfate solution. In this case, a concentration of the lipids was 32 mg/mL, and the lipid solution was stirred for an hour while maintaining the mixing temperature at 60° C. The mixed lipid solution was homogenized through a high-temperature extruder (LIPEX, Evonik). When the high-temperature extruder was used, the liposomes were prepared by reducing step by step the sizes of the liposomes through polycarbonate filters in the extruder from a 0.8-μm pore size to a 0.4-μm or 0.2-μm pore size. This process was repeatedly performed until the size of the prepared liposomes reached 100 nm to 200 nm.

The prepared liposome solution was replaced with a mixed solution of 10% sucrose and 10 mM histidine, and a size exclusive chromatography (SEC) method or a size extrusion chromatography method using FPLC was performed. The SEC was performed at a flow velocity of 10 mL/min using a high-prep 26/10 column.

To encapsulate doxorubicin, doxorubicin and the liposome having compositions listed in Table 11 were then mixed at a mass ratio of 1:8, and stirred at 37° C. for an hour. Thereafter, the non-encapsulated doxorubicin was separated using size extrusion chromatography.

Example 14: Sonosensitivity Test of Liposome Prepared by Ethanol Addition Method A sonosensitivity test on the doxorubicin-encapsulated liposomes prepared by an ethanol addition method was performed using high-intensity focused ultrasound. Compositions of the prepared liposomes are as listed in Table 13. Ultrasound equipment for an ultrasound sensitization test was used in the same manner as in the method performed in Example 2. The conditions for ultrasound released in performing a doxorubicin sonosensitivity test were as follows: doxorubicin was released for 60 seconds using a frequency of 29 kHz and an ultrasound intensity of 92 W/cm$^2$. The released doxorubicin was purified by an SEC method, and quantified using the absorbance at a wavelength of 475 nm.

TABLE 13

Physical properties and sonosensitivity results of liposomes prepared by ethanol addition method

| Sample No. | DSPC | DSPE-PEG2k | Cholesterol | DOPE | MSPC | Size (d. nm), PDI | Zeta potential (mV) | Release (%) |
|---|---|---|---|---|---|---|---|---|
| 1 | 10 | 5 | 5 | 55 | 5 | 141.9, 0.124 | −31.5 ± 7.23 | 69.8 |
| 2 | | | | | 7 | 159.7, 0.115 | −32.6 ± 5.48 | 71.6 |
| 3 | | | | | 10 | 153.6, 0.131 | −32.9 ± 7.9 | 59.6 |
| 4 | | | 10 | | 5 | 143.7, 0.119 | −28.6 ± 6.97 | 62.1 |
| 5 | | | | | 7 | 161.1, 0.102 | −27.9 ± 7.41 | 64.3 |
| 6 | | | | | 10 | 153.5, 0.130 | −27.2 ± 8.51 | 55.5 |
| 7 | | | 15 | | 5 | 146.2, 0.120 | −33.7 ± 8.94 | 54.5 |
| 8 | | | | | 7 | 151.2, 0.114 | −33.7 ± 7.83 | 55.3 |
| 9 | | | | | 10 | 161.3, 0.132 | −33.7 ± 7.57 | 52 |

Example 15: Pharmacokinetics (pK) Test According to Ratio of MSPC

Among the sonosensitive liposomes used in Example 7, liposomes containing MSPC at a molar ratio of 1%, 5%, and 7% were selected to perform a pK test using Sprague-Dawley rats. Compositions of the sonosensitive liposomes used in the pK test are as listed in Table 14.

TABLE 14

Compositions of liposomes used for pK evaluation according to ratio of MSPC

| Sample | DSPC (mol %) | DSPE-PEG2k (mol %) | Cholesterol (mol %) | DOPE (mol %) | MSPC (mol %) |
|---|---|---|---|---|---|
| MSPC-1% | 10 | 5 | 15 | 65 | 1 |
| MSPC-5% | | | | | 5 |
| MSPC-7% | | | | | 7 |

Each of the liposomes was intravenously administered to Sprague-Dawley rats at a dose of 2 mg/kg, and blood was collected through the jugular vein of each rat. The blood collection was performed at time points of 30 minutes, 1, 4, 12, 24, and 48 hours, and an anticoagulant (i.e., sodium heparin) was used to prevent the coagulation of the collected blood. Then, the collected blood was centrifuged at 12,000 rpm for 2 minutes to separate plasma. The quantitative analysis of doxorubicin was performed using LC-MS/MS, and a change in pK according to the ratio of MSPC was evaluated.

Figure 11:
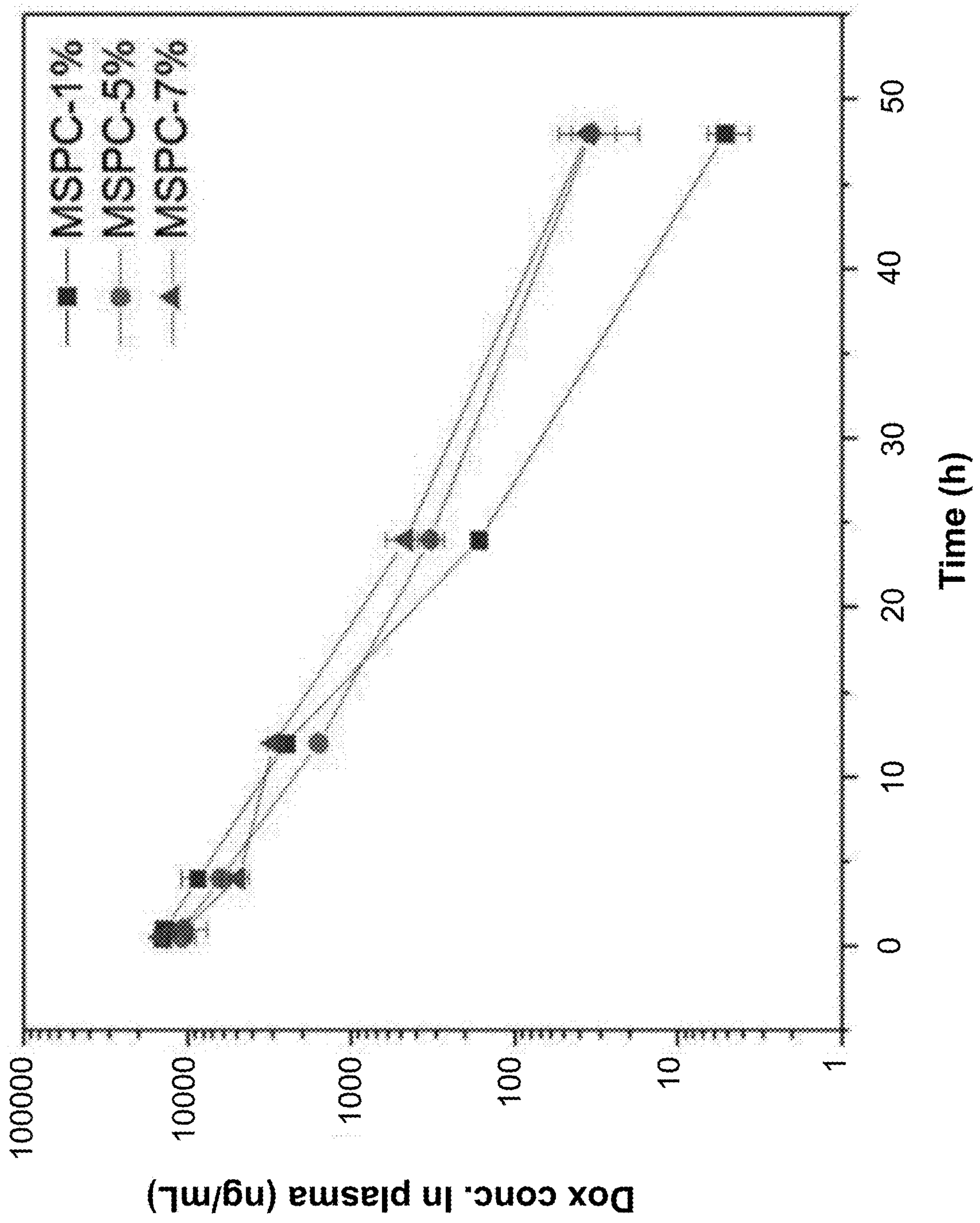
FIG. 11 is a diagram showing a plasma concentration of doxorubicin according to the ratio of MSPC with time, showing that the plasma concentration of doxorubicin according to the ratio of MSPC is determined in a blood pK evaluation test according to one exemplary embodiment of the present invention.

The pK results according to the ratio of MSPC are shown in Table 15 and FIG. 11. As a result, it was confirmed that the volume of the sonosensitive liposome present in the body increased with an increasing ratio of MSPC. When the content of MSPC was 1%, doxorubicin was detected at a concentration of 5.1±1.5 ng/mL after 48 hours. When the content of MSPC was 5% and 7%, doxorubicin was detected at a concentration of 34.4±10.3 and 35.6±17.9, respectively.

Also, when the content of MSPC was 1%, 5%, and 7%, the in vivo half-lives were found to be 4.0±0.1 hours, 6.4±0.9 hours, and 5.7±0.7 hours, respectively. The results support that the in vivo stability was maintained in blood for a long time because the in vivo stability was improved with a higher ratio of MSPC, and the MSPC enhanced the blood stability of the sonosensitive liposome.

TABLE 15 pK test results according to MSPC ratio (MSPC-1%, 5%, and 7%)

| Blood collection | Doxorubicin concentration (ng/mL) | | |
|---|---|---|---|
| time (hr) | MSPC-1% | MSPC-5% | MSPC-7% |
| 0.5 | 13,992.7 ± 805.3 | 10,749.2 ± 1,851.2 | 14,478.3 ± 845.6 |
| 1 | 13,735.7 ± 1,493.6 | 10,618.1 ± 2,992.9 | 10,547.6 ± 1,378.6 |
| 4 | 8,543.0 ± 2,375.2 | 6,266.6 ± 694.7 | 4,878.4 ± 623.7 |
| 12 | 2,493.8 ± 244.3 | 1,582.3 ± 73.1 | 2,942.3 ± 315.5 |
| 24 | 163.8 ± 17.5 | 328.2 ± 60.6 | 463.0 ± 154.8 |
| 48 | 5.1 ± 1.5 | 34.4 ± 10.3 | 35.6 ± 17.9 |

The above description of the present invention has been given by way of illustration only. Therefore, those skilled in the art to which the present invention pertains will appreciate that the present invention can be embodied in other specific forms without changing the technical spirit or essential features of the present invention. Therefore, it should be understood that the embodiments described above are for the purpose of illustration only, and not intended to be limiting in all respects.

INDUSTRIAL APPLICABILITY

It was confirmed that the sonosensitive liposome according to the present invention has high encapsulation efficiency and excellent sonosensitivity and liposome stability, and shows an excellent effect of increasing a drug release rate by sonication compared to the existing commercial drugs, as well as a cancer cell death effect and a cancer cell-penetrating effect. Therefore, the sonosensitive liposome according to the present invention increases the delivery efficiency of an encapsulated drug, and has an improved drug delivery effect when used in combination with sonication to target cancer cells. As a result, the sonosensitive liposome according to the present invention is expected to shows various functions in the fields of cancer treatment and drug delivery carriers. Therefore, the sonosensitive liposome of the present invention is industrially applicable.

The invention claimed is:

1. A sonosensitive liposome comprising a liposome membrane consisting of 1,2-distearoyl-sn-glycero-3-phosphorylcholine (DSPC), 1,2-distearoyl-sn-glycero-3-phosphoethanolamine with conjugated methoxyl poly(ethylene glycol 2000) (DSPE-mPEG2000), 1,2-dioleoyl-sn-glycero-3-phosphoethanolamine (DOPE), cholesterol, and lyso-PC, and wherein the DSPC, the DSPE-mPEG2000, the DOPE, the cholesterol, and the lyso-PC are included at a molar ratio (mol %) of 1 to 40:1 to 9:35 to 80:0.1 to 40:1 to 10, wherein the molar ratio (mol %) is a molar ratio of mol % values, and wherein the mol % values comprise a total number of moles of the DSPC, the DSPE-mPEG2000, the DOPE, the cholesterol, and the lyso-P in the sonosensitive liposome membrane.

2. The sonosensitive liposome of claim 1, wherein the sonosensitive liposome has a drug encapsulated therein.

3. The sonosensitive liposome of claim 2, wherein the drug is an anticancer drug.

4. The sonosensitive liposome of claim 1, wherein the sonosensitive liposome has a particle size of 100 nm to 200 nm.

5. The sonosensitive liposome of claim 3, wherein the anticancer drug comprises one or more selected from the group consisting of doxorubicin, paclitaxel, doxetaxel, cisplatin, Gleevec, 5-fluorouracil (5-FU), tamoxifen, carboplatin, topotecan, belotecan, imatinib, irinotecan, floxuridine, vinorelbine, gemcitabine, leuprolide, flutamide, zoledronate, methotrexate, camptothecin, vincristine, hydroxyurea, streptozotocin, leucovorin, oxaliplatin, valrubicin, retinoic acid, mechlorethamine, chlorambucil, busulfan, doxifluridine, vinblastine, mitomycin, prednisone, Afinitor, and mitoxantrone.

6. The sonosensitive liposome of claim 1, wherein the sonosensitive liposome is prepared by a Preparation Process selected from the group consisting of the following Preparation Processes 1 to 3:

[Preparation Process 1]

(a) dissolving DSPC, DSPE-mPEG2000, DOPE, cholesterol, and lyso-PC in a first organic solvent;

(b) evaporating the organic solvent to prepare a liposome membrane;

(c) hydrating the liposome membrane in an aqueous solution and stirring the liposome membrane solution; and (d) extruding the liposome membrane solution through an extruder;

[Preparation Process 2]

(a) dissolving DSPC, DSPE-mPEG2000, DOPE, cholesterol, and lyso-PC in ethanol;

(b) hydrating the ethanol solution prepared in Step (a) in an aqueous solution and stirring the ethanol solution; and (c) extruding the ethanol solution through an extruder;

[Preparation Process 3]

(a) dissolving DSPC, DSPE-mPEG2000, DOPE, cholesterol, and lyso-PC in a first organic solvent;

(b) mixing the first organic solvent solution prepared in Step (a) and an aqueous solution while changing the flow velocities thereof using a channel of a microfluidic system; and (c) removing the organic solvent.

7. The sonosensitive liposome of claim 6, wherein the first organic solvent comprises one or more selected from the group consisting of dimethylacetamide, dimethylformamide, dimethyl sulfoxide, chloroform, methanol, ethanol, and ether.

8. A method of treating cancer, comprising:

administering an effective amount of the sonosensitive liposome of claim 1 to a subject; and treating the sonosensitive liposome with ultrasound;

wherein the sonosensitive liposome has an anticancer drug encapsulated therein, and wherein the cancer is one or more selected from the group consisting of breast cancer, colon cancer, lung cancer, small-cell lung cancer, gastric cancer, liver cancer, blood cancer, bone cancer, pancreatic cancer, skin cancer, head cancer, neck cancer, skin melanoma, intraocular melanoma, uterine cancer, ovarian cancer, rectal cancer, anal cancer, colorectal cancer, fallopian tube carcinoma, endometrial carcinoma, cervical cancer, vaginal cancer, vulva carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureteral cancer, renal cell carcinoma, renal pelvic carcinoma, CNS tumors, primary CNS lymphoma, spinal cord tumors, brainstem glioma, and pituitary adenoma.

* * * * *